(12) United States Patent
Bernardon et al.

(10) Patent No.: US 6,258,775 B1
(45) Date of Patent: Jul. 10, 2001

(54) BI-AROMATIC COMPOUNDS, PHARMACEUTICAL AND COSMETIC COMPOSITIONS CONTAINING SAME AND USES

(75) Inventors: Jean-Michel Bernardon, Le Rouret; Philippe Diaz, Nice, both of (FR)

(73) Assignee: Centre International de Recherches Dermatologiques Galderma, Valbonne (FR)

( * ) Notice: Subject to any disclaimer, the term of this patent is extended or adjusted under 35 U.S.C. 154(b) by 0 days.

(21) Appl. No.: 09/101,622

(22) PCT Filed: Nov. 17, 1998

(86) PCT No.: PCT/FR97/02063

§ 371 Date: Sep. 4, 1998

§ 102(e) Date: Sep. 4, 1998

(87) PCT Pub. No.: WO98/22423

PCT Pub. Date: May 28, 1998

(30) Foreign Application Priority Data

Nov. 19, 1996 (FR) .................................................. 96 14098

(51) Int. Cl.[7] .......................... A61K 38/00; A61K 31/19; C07C 33/38; C07C 59/84; C07D 295/185; C07D 339/08

(52) U.S. Cl. ................................ 514/2; 514/18; 514/336; 514/345; 514/433; 514/444; 514/445; 514/452; 514/473; 514/475; 546/268.4; 546/290; 549/59; 549/62; 549/475; 549/483; 549/331; 549/14; 549/357; 564/253; 564/254; 564/300; 568/27; 568/28; 536/55.2; 424/70; 540/1

(58) Field of Search .................... 514/2, 18, 54, 514/62, 345, 433, 444, 445, 452, 473, 475; 534/55.2; 546/268.4, 290; 424/70; 549/14, 59, 62, 331, 357, 475, 483; 560/100; 564/253, 254, 300; 568/27, 28

(56) References Cited

U.S. PATENT DOCUMENTS 4,833,240 * 5/1989 Maignan et al. .................... 536/55.2

5,013,352 * 5/1991 Markley et al. .......................... 71/94
5,476,873 * 5/1991 Brooks et al. ....................... 514/595

FOREIGN PATENT DOCUMENTS

| 0 260 162 | 3/1988 | (EP) . |
| 2 278 331 | 1/1974 | (FR) . |
| 2 371 195 | 11/1976 | (FR) . |
| 2 228 734 | 9/1990 | (GB) . |
| 1581359 | 12/1989 | (HU) . |
| WO 92/00076 | 1/1992 | (WO) . |

OTHER PUBLICATIONS

Kuo–Long Yu: "Application of the Heck reaction in the synthesis of truncated naphthoic acid retinoids", Bioorganic & Medicinal Chemistry Letters, vol. 6, No. 23, 1996, pp. 2859–2864, XP002061556.

Uspatfull 95:112558 to US Pat No. 5476873 and Reg. No. 141581–11–5, Dec. 1995.*

* cited by examiner

Primary Examiner—Bennett Celsa
(74) Attorney, Agent, or Firm—Burns, Doane, Swecker & Mathis, L.L.P.

(57) ABSTRACT

The invention relates to novel biaromatic compounds having general formula I

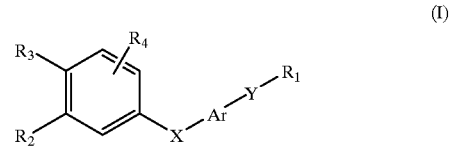

and their use in pharmaceutical compositions for use in human and veterinary medicine, in particular for treating dermatological, rheumatic, respiratory, cardiovascular, and ophthalmological disorders, and for use in cosmetic compositions.

25 Claims, 2 Drawing Sheets

BI-AROMATIC COMPOUNDS, PHARMACEUTICAL AND COSMETIC COMPOSITIONS CONTAINING SAME AND USES

BRIEF DESCRIPTION OF THE INVENTION

The invention relates to biaromatic compounds, as novel and useful industrial products. The invention also relates to the use of these novel compounds in pharmaceutical compositions intended for use in human or veterinary medicine, or alternatively in cosmetic compositions.

The compounds according to the invention have pronounced activity in the fields of cell differentiation and proliferation, and find applications more particularly in the topical and systemic treatment of dermatological complaints associated with a keratinization disorder, dermatological (or other) complaints with an inflammatory and/or immunoallergic component, and dermal or epidermal proliferations, whether these are benign or malignant. These compounds can also be used in the treatment of degenerative diseases of connective tissue, to combat ageing of the skin, both photoinduced and chronological ageing, and to treat cicatrization problems. They moreover find an application in the ophthalmological field, in particular in the treatment of corneopathies.

Figure 1:
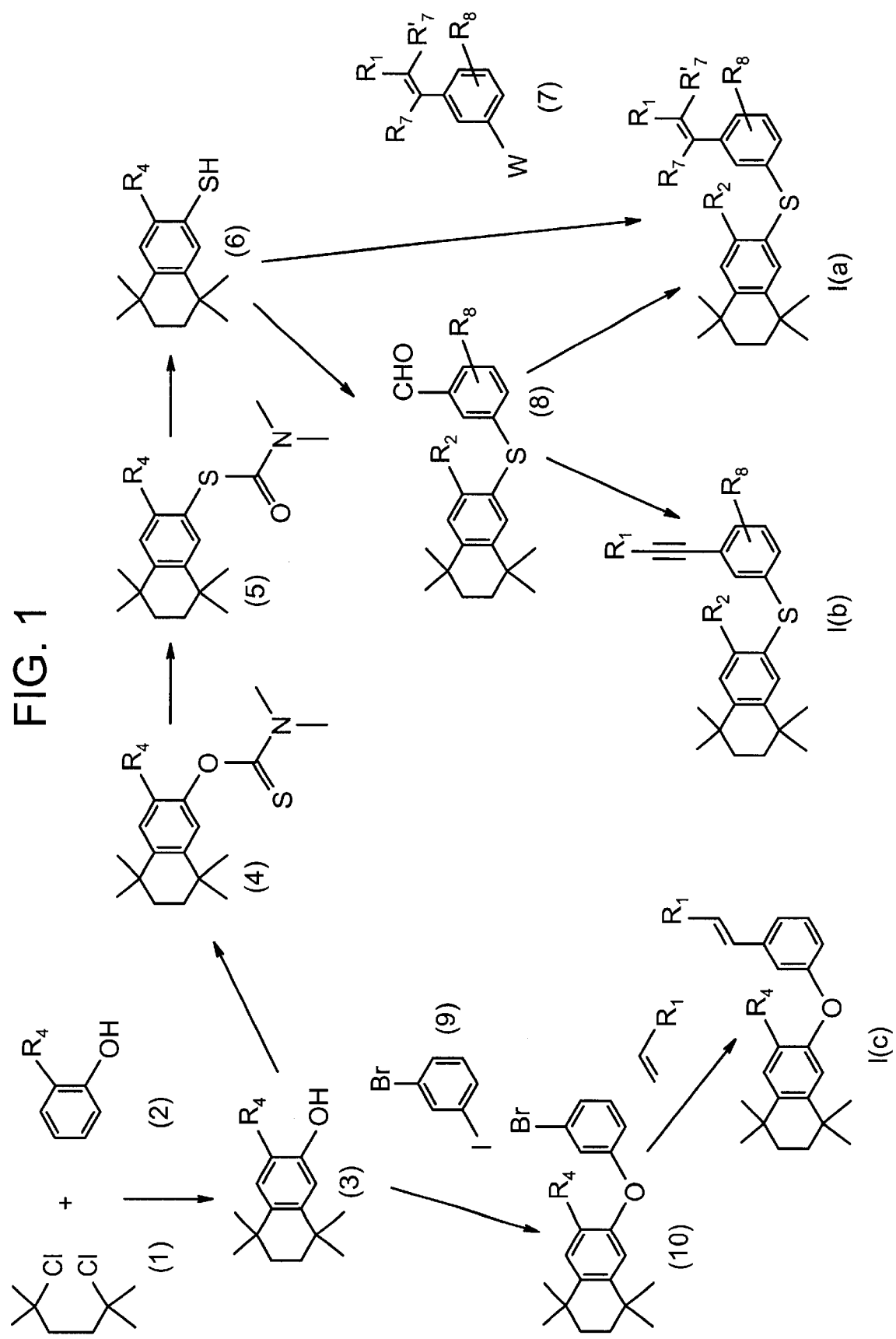
FIGS. 1 and 2 contain reaction schemes for synthesis of compounds according to the invention.

The compounds according to the invention can also be used in cosmetic compositions for hair and body hygiene.

DETAILED DESCRIPTION OF THE INVENTION

The present invention relates to compounds [lacuna] can be represented by the general formula (I) below:

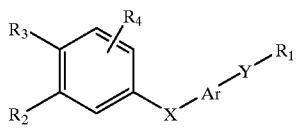

(I)

in which:
—$R_1$ represents
(i) the radical —$CH_3$,
(ii) the radical —$CH_2$—O—$R_5$,
(iii) the radical —O—$R_5$,
(iv) the radical —CO—$R_6$,
$R_5$ and $R_6$ having the meanings given below,
Y represents a radical chosen from the radicals of formulae (a) and (b) below:

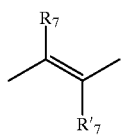

(a)

(b)

$R_7$ and $R'_7$ having the meanings given below,

Ar represents a radical chosen from the radicals of formulae (c) to (f) below:

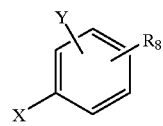

(c)

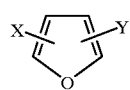

(d)

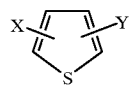

(e)

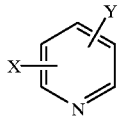

(f)

in which the radical Y is in an ortho or meta position relative to the radical X, X and Y of these formulae corresponding to X and Y represented in formula (I), $R_8$ having the meaning given below, X represents an oxygen or sulphur atom, a radical —SO—, —$SO_2$—, —N($R_9$)— or a radical chosen from the radicals of formulae (g) to (r) below:

(g)

(h)

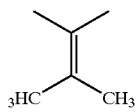

(i)

(j)

(k)

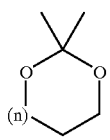 (l)

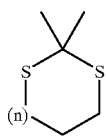 (m)

 (n)

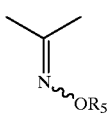 (o)

 (p)

 (q)

 (r)

$R_5$, $R_9$, $R_{12}$ and n having the meanings given below, $R_2$ and $R_3$, which may be identical or different, are chosen from the group consisting of:

(i) a hydrogen atom, (ii) an alkyl radical having at least 3 carbon atoms, among which the carbon attached to the phenyl radical of formula (I) is substituted with at least two carbon atoms, (iii) a linear or branched alkyl radical, (iv) a radical —$OR_5$, (v) a radical —$SR_5$, (vi) a polyether radical, $R_5$ having the meaning given below, it being understood that $R_2$ and $R_3$, taken together, can form, with the adjacent aromatic ring, a 5- or 6-membered ring, optionally substituted with methyl groups and/or optionally interrupted by an oxygen or sulphur atom, it being understood that, when $R_2$ and $R_3$ do not form a ring, at least one of the radicals $R_2$ and $R_3$ has a meaning (ii) mentioned above, $R_4$ and $R_8$, which may be identical or different, represent a hydrogen atom, a halogen atom, a linear or branched alkyl radical, or a radical —$OR_5$, a polyether radical, $R_5$ represents a hydrogen atom, a lower alkyl radical or a radical —$COR_{10}$, $R_{10}$ having the meaning given below, $R_6$ represents:

(a) a hydrogen atom (b) a lower alkyl radical (c) a radical of formula:

R' and R" having the meanings given below, (d) a radical —$OR_{11}$ $R_{11}$ having the meaning given below, $R_7$, $R'_7$ and $R_9$, which may be identical or different, represent a hydrogen atom or a lower alkyl radical, n is an integer equal to 0 or 1, $R_{10}$ represents a lower alkyl radical, $R_{11}$ represents a hydrogen atom, a linear or branched alkyl radical, an alkenyl radical, a mono- or polyhydroxyalkyl radical, an aryl or aralkyl radical, optionally substituted, a sugar residue or an amino acid or peptide residue, $R_{12}$ represents a lower alkyl radical, R' and R", which may be identical or different, represent a hydrogen atom, a lower alkyl radical, a mono- or polyhydroxyalkyl radical, an optionally substituted aryl radical, or an amino acid, peptide or sugar residue, or alternatively, taken together, form a heterocycle, and the optical and geometrical isomers of the said compounds of formula (I), as well as their salts.

When the compounds according to the invention are in the form of salts, by addition of an acid, they are pharmaceutically or cosmetically acceptable salts obtained by addition of an inorganic or organic acid, in particular hydrochloric acid, sulphuric acid, acetic acid, citric acid, fumaric acid, hemisuccinic acid, maleic acid or mandelic acid. When the compounds according to the invention are in the form of salts by addition of a base, they are preferably salts of an alkali metal or alkaline-earth metal or alternatively of zinc or of an organic amine.

According to the present invention, the expression linear or branched alkyl radical is understood to refer to a linear or branched radical optionally substituted with one or more halogen atoms, having from 1 to 20, preferably from 1 to 12, carbon atoms, advantageously the methyl, ethyl, isopropyl, butyl, tert-butyl, hexyl, nonyl and dodecyl radicals. When it is lower, the alkyl radical generally comprises from 1 to 6 carbon atoms. A methyl, ethyl, isopropyl, tert-butyl or hexyl radical is preferred.

Among the linear alkyl radicals having from 1 to 20 carbon atoms, mention may be made in particular of the methyl, ethyl, propyl, 2-ethylhexyl, octyl, dodecyl, hexadecyl and octadecyl radicals.

Among the branched alkyl radicals having from 1 to 20 carbon atoms, preferably from 3 to 20 carbon atoms, mention may be made in particular of the 2-methylbutyl, 2-methylpentyl, 1-methylhexyl and 3-methylheptyl radicals.

Among the alkyl radicals having at least 3 carbon atoms, among which the carbon attached to the phenyl radical of formula (I) is substituted with at least two carbon atoms, mention may be made of the isopropyl, tert-butyl, 1,1-dimethylhexyl and 1,1-dimethyldecyl radicals. Preferably, these radicals have not more than 20 carbon atoms, even more preferably not more than 12 carbon atoms. Advantageously, the radical (ii) is the tert-butyl radical.

The term alkenyl radical is understood to refer to a linear or branched radical having from 2 to 20 carbon atoms and containing one or more double bonds.

Among the alkenyl radicals, a radical containing from 2 to 5 carbon atoms and having one or more ethylenic unsaturations, more particularly such as the allyl radical, is preferred.

The terms monohydroxyalkyl radical and polyhydroxyalkyl radical should be understood to refer to a radical containing from 1 to 6 carbon atoms and from 1 to 5 hydroxyl groups.

Among the polyhydroxyalkyl radicals, a radical having from 3 to 6 carbon atoms and from 2 to 5 hydroxyl groups, such as the 2,3-dihydroxypropyl, 2,3,4-trihydroxybutyl and 2,3,4,5-tetrahydroxypentyl radicals or the pentaerythritol residue, is preferred.

Among the optionally substituted aryl radicals, a phenyl radical optionally substituted with at least one halogen atom, a hydroxyl radical, an alkyl radical, a nitro function, a methoxy group or an optionally substituted amine function is preferred.

Among the optionally substituted aralkyl radicals, the benzyl or phenethyl radical optionally substituted with at least one halogen atom, a hydroxyl radical, a nitro function or a methoxy group is preferred.

The term sugar residue is understood to refer to a residue derived in particular from glucose, from galactose or from mannose, or alternatively from glucuronic acid.

The term amino acid residue is understood to refer in particular to a residue derived from one of the amino acids such as lysine, glycine or aspartic acid, and the term peptide residue is understood to refer more particularly to a dipeptide or tripeptide residue resulting from the combination of amino acids.

The term heterocycle is understood to refer preferably to a piperidino, morpholino, pyrrolidino or piperazino radical, optionally substituted in position 4 with a $C_1$–$C_6$ alkyl or a polyhydroxyalkyl radical as defined above.

Among the polyether radicals, a radical containing from 2 to 6 carbon atoms, in particular the methoxymethoxy, methoxyethoxy, methoxyethoxymethoxy, methoxymethoxyethyl, methoxymethoxypropyl and methoxyhexyloxy radicals, is preferred.

When the radicals $R_4$ and $R_8$ represent a halogen atom, it is preferably a fluorine, bromine or chlorine atom.

Among the compounds of formula (I) above falling within the context of the present invention, mention may be made in particular of the following:

3-[3-(5,5,8,8-Tetramethyl-5,6,7,8-tetrahydro-2-naphthylcarbonyl)phenyl]acrylic acid.

3-[3-(3,5,5,8,8-Pentamethyl-5,6,7,8-tetrahydro-2-naphthylcarbonyl)phenyl]acrylic acid.

3-[3-(3,5,5,8,8-Pentamethyl-5,6,7,8-tetrahydro-2-naphthylthio)phenyl]acrylic acid.

3-[3-(5,5,8,8-Tetramethyl-5,6,7,8-tetrahydro-2-naphthylthio)phenyl]acrylic acid.

Ethyl 3-{2-[1-(3,5,5,8,8-pentamethyl-5,6,7,8-tetrahydro-2-naphthyl)vinyl]phenyl}acrylate.

3-{2-[1-(3,5,5,8,8-Pentamethyl-5,6,7,8-tetrahydro-2-naphthyl)vinyl]phenyl}acrylic acid.

Ethyl 3-{3-[1-(3,5,5,8,8-pentamethyl-5,6,7,8-tetrahydro-2-naphthyl)vinyl]phenyl}acrylate.

3-{3-[1-(3,5,5,8,8-Pentamethyl-5,6,7,8-tetrahydro-2-naphthyl)vinyl]phenyl}acrylic acid.

Ethyl 3-{2-[1-(5,5,8,8-tetramethyl-5,6,7,8-tetrahydro-2-naphthyl)vinyl]phenyl}acrylate.

3-{2-[1-(5,5,8,8-Tetramethyl-5,6,7,8-tetrahydro-2-naphthyl)vinyl]phenyl}acrylic acid.

Ethyl 3-{3-[1-(5,5,8,8-tetramethyl-5,6,7,8-tetrahydro-2-naphthyl)vinyl]phenyl}acrylate.

3-{3-[1-(5,5,8,8-Tetramethyl-5,6,7,8-tetrahydro-2-naphthyl)vinyl]phenyl}acrylic acid.

Ethyl 3-{3-[1-(5,5,8,8-tetramethyl-5,6,7,8-tetrahydro-2-naphthyl)ethyl]phenyl}acrylate.

3-{3-[1-(5,5,8,8-Tetramethyl-5,6,7,8-tetrahydro-2-naphthyl)ethyl]phenyl}acrylic acid.

Ethyl 3-{2-[1-(5,5,8,8-tetramethyl-5,6,7,8-tetrahydro-2-naphthyl)ethyl]phenyl}acrylate.

3-{2-[1-(5,5,8,8-Tetramethyl-5,6,7,8-tetrahydro-2-naphthyl)ethyl]phenyl}acrylic acid.

Ethyl 3-{2-[1-(3,5,5,8,8-pentamethyl-5,6,7,8-tetrahydro-2-naphthyl)ethyl]phenyl}acrylate.

3-{2-[1-(3,5,5,8,8-Pentamethyl-5,6,7,8-tetrahydro-2-naphthyl)ethyl]phenyl}acrylic acid.

Ethyl 3-{3-[1-(3,5,5,8,8-Pentamethyl-5,6,7,8-tetrahydro-2-naphthyl)ethyl]phenyl}acrylate.

3-{3-[1-(3,5,5,8,8-Pentamethyl-5,6,7,8-tetrahydro-2-naphthyl)ethyl]phenyl}acrylic acid.

Ethyl 3-{2-[1-(5,5,8,8-tetramethyl-5,6,7,8-tetrahydro-2-naphthyl)cyclopropyl]phenyl}acrylate.

3-{2-[1-(5,5,8,8-Tetramethyl-5,6,7,8-tetrahydro-2-naphthyl)cyclopropyl]phenyl}acrylic acid.

Ethyl 3-{3-[1-(5,58,8-tetramethyl-5,6,7,8-tetrahydro-2-naphthyl)cyclopropyl]phenyl}acrylate.

3-{3-[1-(5,5,8,8-Tetramethyl-5,6,7,8-tetrahydro-2-naphthyl)cyclopropyl]phenyl}acrylic acid.

Ethyl 3-{3-[hydroxyimino-(3,5,5,8,8-penta-methyl-5,6,7,8-tetrahydro-2-naphthyl)methyl]phenyl}-acrylate.

3-{3-[Hydroxyimino-(3,5,5,8,8-pentamethyl-5,6,7,8-tetrahydro-2-naphthyl)methyl]phenyl}acrylic acid.

Ethyl 3-{3-[hydroxyimino-(5,5,8,8-tetramethyl-5,6,7,8-tetrahydro-2-naphthyl)methyl]phenyl}-acrylate.

3-{3-[Hydroxyimino-(3,5,5,8,8-pentamethyl-5,6,7,8-tetrahydro-2-naphthyl)methyl]phenyl}acrylic acid.

Ethyl 3-{3-[2-(3,5,5,8,8-pentamethyl-5,6,7,8-tetrahydro-2-naphthyl)-[1,3]-dithian-2-yl]phenyl}-acrylate.

3-{3-[2-(3,5,5,8,8-Pentamethyl-5,6,7,8-tetrahydro-2-naphthyl)-[1,3]-dithian-2-yl]phenyl}acrylic acid.

3-{3-[Hydroxylamine-(3,5,5,8,8-pentamethyl-5,6,7,8-tetrahydro-2-naphthyl)methyl]phenyl}acrylic acid.

Ethyl 3-{3-[hydroxylamine-(5,5,8,8-tetramethyl-5,6,7,8-tetrahydro-2-naphthyl)methyl]phenyl}-acrylate.

3-{2-[Hydroxylamine-(3,5,5,8,8-pentamethyl-5,6,7,8-tetrahydro-2-naphthyl)methyl]phenyl}acrylic acid.

Ethyl 3-{2-[Hydroxylamine-(5,5,8,8-tetramethyl-5,6,7,8-tetrahydro-2-naphthyl)methyl]phenyl}-acrylate.

{3-[1-(5,5,8,8-Tetramethyl-5,6,7,8-tetrahydro-2-naphthyl)cyclopropyl]phenyl}propynoic acid.

{3-[1-(3,5,5,8,8-Pentamethyl-5,6,7,8-tetrahydro-2-naphthyl)cyclopropyl]phenyl}propynoic acid.

{2-[1-(5,5,8,8-Tetramethyl-5,6,7,8-tetrahydro-2-naphthyl)cyclopropyl]phenyl}propynoic acid.

{2-[1-(3,5,5,8,8-Pentamethyl-5,6,7,8-tetrahydro-2-naphthyl)cyclopropyl]phenyl}propynoic acid.

3-{2-[1-(3,5,5,8,8-Pentamethyl-5,6,7,8-tetrahydro-2-naphthyl)cyclopropyl]phenyl}acrylic acid.

3-{3-[1-(3,5,5,8,8-Pentamethyl-5,6,7,8-tetrahydro-2-naphthyl)cyclopropyl]phenyl}acrylic acid.

3-{4-Hydroxy-3-[1-(5,5,8,8-tetramethyl-5,6,7,8-tetrahydro-2-naphthyl)cyclopropyl]phenyl}-acrylic acid.

3-{3-Hydroxy-2-[1-(5,5,8,8-tetramethyl-5,6,7,8-tetrahydro-2-naphthyl)cyclopropyl]phenyl}-acrylic acid.

3-{3-[1-(5,5,8,8-Tetramethyl-5,6,7,8-tetrahydro-2-naphthyl)cyclopropyl]-4-methoxyphenyl}acrylic acid.

3-{2-[1-(5,5,8,8-Tetramethyl-5,6,7,8-tetrahydro-2-naphthyl)cyclopropyl]-3-methoxyphenyl}acrylic acid.

3-{4-Hydroxy-3-[1-(3,5,5,8,8-pentamethyl-5,6,7,8-tetrahydro-2-naphthyl)cyclopropyl]phenyl}-acrylic acid.

3-{3-Hydroxy-2-[1-(3,5,5,8,8-pentamethyl-5,6,7,8-tetrahydro-2-naphthyl)cyclopropyl]phenyl}-acrylic acid.

3-{3-[1-(3,5,5,8,8-Pentamethyl-5,6,7,8-tetrahydro-2-naphthyl)cyclopropyl]-4-methoxyphenyl}acrylic acid.

3-{2-[1-(3,5,5,8,8-Pentamethyl-5,6,7,8-tetrahydro-2-naphthyl)cyclopropyl]-3-methoxyphenyl}acrylic acid.

3-{3-[1-(5,5,8,8-Tetramethyl-5,6,7,8-tetrahydro-2-naphthyl)cyclopropyl]phenyl}acrylamide.

3-{2-[1-(5,5,8,8-Tetramethyl-5,6,7,8-tetrahydro-2-naphthyl)cyclopropyl]phenyl}acrylamide.

3-{3-[1-(3,5,5,8,8-Pentamethyl-5,6,7,8-tetrahydro-2-naphthyl)cyclopropyl]phenyl}acrylamide.

3-{2-[1-(5,5,8,8-Pentamethyl-5,6,7,8-tetrahydro-2-naphthyl)cyclopropyl]phenyl}acrylamide.

N-Ethyl-3-{3-[1-(5,5,8,8-tetramethyl-5,6,7,8-tetrahydro-2-naphthyl)cyclopropyl]phenyl}acrylamide.

N-Ethyl-3-{2-[1-(5,5,8,8-tetramethyl-5,6,7,8-tetrahydro-2-naphthyl)cyclopropyl]phenyl}acrylamide.

N-Ethyl-3-{3-[1-(3,5,5,8,8-pentamethyl-5,6,7,8-tetrahydro-2-naphthyl)cyclopropyl]phenyl}-acrylamide.

N-Ethyl-3-{2-[1-(3,5,5,8,8-pentamethyl-5,6,7,8-tetrahydro-2-naphthyl)cyclopropyl]phenyl}-acrylamide.

b 1-Morpholin-4-yl-3-{3-[1-(5,5,8,8-tetramethyl-5,6,7,8-tetrahydro-2-naphthyl)cyclopropyl]-phenyl}propenone.

1-Morpholin-4-yl-3-{2-[1-(5,5,8,8-tetramethyl-5,6,7,8-tetrahydro-2-naphthyl)cyclopropyl]-phenyl}propenone.

1-Morpholin-4-yl-3-{3-[1-(3,5,5,8,8-pentamethyl-5,6,7,8-tetrahydro-2-naphthyl)cyclopropyl]-phenyl}propenone.

1-Morpholin-4-yl-3-{2-[1-(3,5,5,8,8-pentamethyl-5,6,7,8-tetrahydro-2-naphthyl)cyclopropyl]-phenyl}propenone.

N-(4-Hydroxyphenyl)-3-{3-[1-(5,5,8,8-tetramethyl-5,6,7,8-tetrahydro-2-naphthyl)cyclopropyl]-phenyl}acrylamide.

N-(4-Hydroxyphenyl)-3-{2-[1-(5,5,8,8-tetramethyl-5,6,7,8-tetrahydro-2-naphthyl)cyclopropyl]-phenyl}acrylamide.

N-(4-Hydroxyphenyl)-3-{3-[1-(3,5,5,8,8-pentamethyl-5,6,7,8-tetrahydro-2-naphthyl)cyclopropyl]-phenyl}acrylamide.

N-(4-Hydroxyphenyl)-3-{2-[1-(3,5,5,8,8-pentamethyl-5,6,7,8-tetrahydro-2-naphthyl)cyclopropyl]-phenyl}acrylamide.

3-{3-[1-(5,5,8,8-Tetramethyl-5,6,7,8-tetrahydro-2-naphthyl)ethyl]phenyl}propenal.

3-{2-[1-(5,5,8,8-Tetramethyl-5,6,7,8-tetrahydro-2-naphthyl)ethyl]phenyl}propenal.

3-{3-[1-(3,5,5,8,8-Pentamethyl-5,6,7,8-tetrahydro-2-naphthyl)ethyl]phenyl}propenal.

3-{2-[1-(3,5,5,8,8-Pentamethyl-5,6,7,8-tetrahydro-2-naphthyl)ethyl]phenyl}propenal.

3-{3-[1-(5,5,8,8-Tetramethyl-5,6,7,8-tetrahydro-2-naphthyl)ethyl]phenyl}prop-2-en-1-ol.

3-{2-[1-(5,5,8,8-Tetramethyl-5,6,7,8-tetrahydro-2-naphthyl)ethyl]phenyl}prop-2-en-1-ol.

3-{3-[1-(3,5,5,8,8-Pentamethyl-5,6,7,8-tetrahydro-2-naphthyl)ethyl]phenyl}prop-2-en-1-ol.

3-{2-[1-(3,5,5,8,8-Pentamethyl-5,6,7,8-tetrahydro-2-naphthyl)ethyl]phenyl}prop-2-en-1-ol.

According to the present invention, the compounds of formula (I) more particularly preferred are those for which at least one, and preferably all, of the conditions below are satisfied:

$R_1$ represents the radical —CO—$R_6$

Ar represents the radicals of formula (c) or (f)

X represents the radicals of formula (g), (h), (n) or (m), $R_2$ and $R_3$ form, together with the adjacent aromatic ring, a 5- or 6-membered ring optionally substituted with methyl groups and/or optionally interrupted by an oxygen or sulphur atom.

Figure 2:
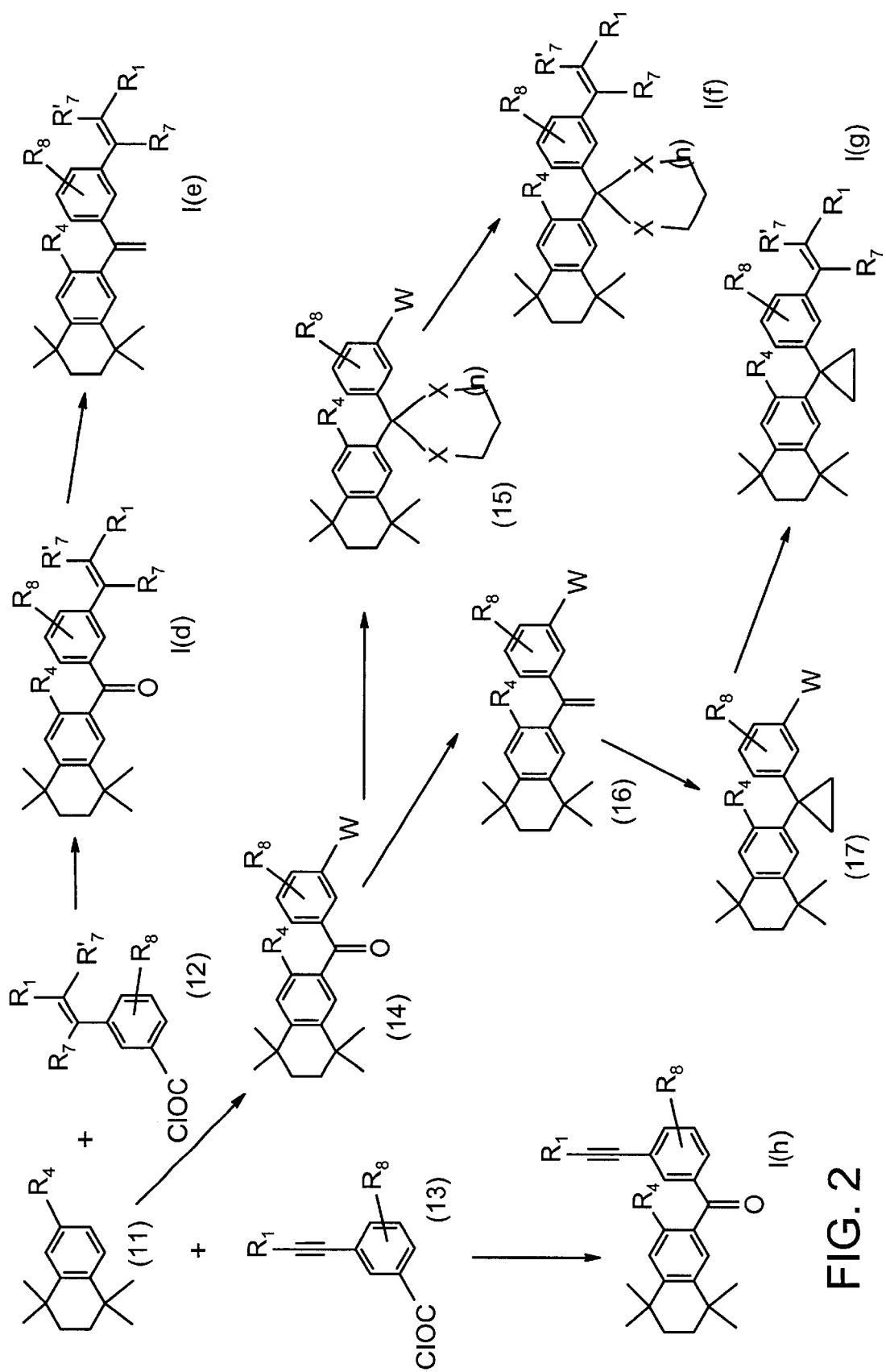

The subject of the present invention is also processes for the preparation of the compounds of formula (I), in particular according to the reaction schemes given in FIGS. 1 and 2.

The compounds of formula I(a) can be obtained (FIG. 1) from the sodium or potassium salt of the thiol derivatives (6) by coupling with halo derivatives (7), preferably a bromo or iodo derivative, in the presence of a catalyst such as certain transition metal complexes, in an alcoholic solvent such as ethyl or butyl alcohol. As catalyst, mention may be made in particular of those derived from nickel or from palladium, for example complexes of Ni(II) with various phosphines and tetrakis(triphenylphosphine)-palladium(0).

The thiol derivatives (6) which can be obtained from the phenolic derivatives (3) via the dialkyl thiocarbamate derivatives (4) and (5) according to the general conditions described by M. Newman and H. Karnes in J. Org. Chem. 1966 31 3980–4.

The phenolic derivatives (3) which can be obtained by a Friedel-Crafts type reaction starting with a phenol (2) and a dihalo derivative (1) in the presence of a Lewis acid, for example aluminium chloride.

The derivatives of formula I(a), when $R_1$ is an acid function, can also be obtained from derivatives (8) via a Horner-Emmons type reaction with triethyl phosphonoacetate in the presence of a base such as sodium hydride, followed by saponification of the ester function with sodium hydroxide or potassium hydroxide in an alcoholic solvent.

The compounds of formula I(b) can be obtained (FIG. 1) from the benzaldehyde derivatives (8) by conversion of the aldehyde function into an acetylene function, for example using the Corey-Fuchs reaction, followed by lithiation and reaction with, for example, ethyl chloroformate, $CO_2$. The derivatives (8) can be obtained from the sodium or potassium salt of the thiol derivatives (6) by coupling with benzaldehyde derivatives, preferably a bromo or iodo derivative, in the presence of a catalyst such as certain transition metal complexes, in an alcoholic solvent such as ethyl or butyl alcohol.

The compounds of formula I(c) can be obtained (FIG. 1) by a Heck-type reaction between halo derivatives (10) and acrylic acid esters in the presence of triethylamine or potassium carbonate and palladium acetate and triphenylphosphine. The derivatives (10) can be obtained by coupling the sodium salt of the phenolic derivatives (3) with halo derivatives (9), preferably an iodo derivative, in the presence of a complex of copper bromide and dimethyl sulphide in a solvent such as pyridine.

The derivatives of formula I(d) and I(h) can be obtained (FIG. 2) from the derivatives (11) by a Friedel-Crafts type reaction with, respectively, the acid chlorides (12) and (13), in a solvent such as dichloromethane, in the presence of aluminium chloride.

The derivatives of formula I(e) can be obtained (FIG. 2) from the derivatives I(d) by a Wittig-type reaction, using methyltriphenylphosphonium bromide in the presence of a base such as potassium tert-butoxide or potassium hexamethyldisilazide.

The derivatives of formula I(f) and I(g) can be obtained (FIG. 2) by a Heck-type reaction between, respectively, the halo derivatives (15) and (16) and acrylic acid esters. The derivatives (15) can be obtained by acetalization or thioacetalization of the keto derivatives (14), for example using ethanedithiol or propanedithiol in dichloromethane in the presence of a catalyst such as boron trifluoride etherate, or using ethylene glycol or propylene glycol in an aromatic solvent such as toluene, in the presence of paratoluenesulphonic acid.

The derivatives (14) can be obtained by a Friedel-Crafts type reaction between the derivatives (11) and halo acid chlorides, more particularly iodo acid chlorides.

The derivatives (17) can be obtained from the keto derivatives (14) firstly by a Wittig reaction using methyltriphenylphosphonium bromide in the presence of a base such as potassium tert-butoxide or potassium hexamethyldisilazide, and then by cyclopropanation, or by using chloroiodomethane and diethylzinc or diiodomethane and zinc.

When $R_1$ represents the —COOH radical, the compounds are preferably prepared by protecting $R_1$ with a protecting group of allylic, benzylic or tert-butyl type.

Passage to the free form can be carried out:

in the case of an allylic protecting group, using a catalyst such as certain transition metal complexes in the presence of a secondary amine, in the case of a benzylic protecting group, by debenzylation in the presence of hydrogen, using a catalyst such as palladium-on-charcoal, in the case of a tert-butyl protecting group, using trimethylsilyl iodide.

When $R_1$ represents an alcohol function, the compounds can be obtained from the corresponding aldehyde derivatives by the action of an alkali metal hydride, such as sodium borohydride, in an alcoholic solvent (for example methanol), or by coupling of the corresponding halo derivative with a derivative of 3-(tributyltin)allyl alcohol.

When $R_1$ represents an aldehyde function, the compounds can be obtained from alcohol derivatives by oxidation in the presence of manganese oxide, pyridinium dichromate or the Swern reagent.

When $R_1$ represents an amide function, the compounds can be obtained from corresponding carboxylic derivatives by reaction with aliphatic, aromatic or heterocyclic amines, either via an acid chloride or in the presence of dicyclohexylcarbodiimide or carbonyldiimidazole.

The products of general formula (I) can be used as starting materials for the manufacture of other compounds of general.;formula (I). These derivatives are obtained according to the standard synthetic methods used in chemistry, such as those described in "Advanced Organic Chemistry" by J. March; John Willey and Sons, 1985.

For example, functional modifications of the group $R_1$ can be carried out as indicated below:

| | | |
|---|---|---|
| carboxylic acid | → | ester |
| ester | → | carboxylic acid |
| acid | → | acid chloride |
| acid chloride | → | amide |
| acid | → | amide |
| acid | → | alcohol |
| alcohol | → | aldehyde |
| amide | → | amine |
| thiol | → | thioether |
| thioether | → | sulphoxide |
| thioether | → | sulphone |
| sulphonic acid | → | sulphonic ester |
| sulphonic acid | → | sulphonamide |
| sulphinic acid | → | sulphinic ester |

These compounds bind to RXR receptors, some of them having agonist activity, others having antagonist activity.

The properties of binding and of transactivation as-RXR receptor agonists, are determined by methods known in the art, such as, for example: Martin, B. et al., Skin Pharmacol., 1992, 5, 57–65; Cavey, M. T. et al., Anal. Biochem., 1990, 186, 19–23; Levin et al., Nature 1992, 355, 359–61; Allenby et al., Proc. Natl. Acad. Sci., 1993, 90, 30–4; Allenby et al., J. Biol. Chem., 1994, 269, 16689–95.

The RXR-agonist activity is also determined by the test as described in French patent application No. 95/07301 filed on Jun. 19, 1995 by the Applicant.

This test comprises the following steps: (i) a sufficient amount of a compound which is an active ligand for at least one receptor of the superfamily of steroidal/thyroidal nuclear receptors other than a ligand specific for the RXR receptors and which can heterodimerize with the RXRs, such as an RAR-agonist molecule, is applied topically to a part of a mammal's skin, (ii) a molecule capable of displaying RXR-agonist activity is administered systemically or topically to this same part of the mammal's skin before, during or after the step (i), and (iii) the response on the part of the mammal's skin thus treated is evaluated. Thus, the response to a topical application to a mammal's ear of an RAR-agonist molecule, which corresponds to an increase in the thickness of this ear, can be increased by systemically or topically administering an RXR receptor agonist-molecule.

The RXRα-antagonist activity is evaluated in the transactivation test by determining the dose ($IC_{50}$) which inhibits by 50% the transactivating activity of a selective RXRα agonist: 6-(3,5,5,8,8-pentamethyl-5,6,7,8-tetrahydro-2-nathphylthio)nicotinic acid (CD 2809) according to the following procedure:

Hela cells are co-transfected with an expression vector coding for RXRα (p565-RXRα) and a reporter plasmid containing the response element 1/2 CRBP II cloned upstream of the heterologous promoter of thymidine kinase and of the reporter gene for chloramphenicom-acetyltransferase (CAT). Eighteen hours after co-transfection, the cells are treated with a fixed concentration of CD 2809 and increasing concentrations of the molecule to be evaluated. After treatment for twenty-four hours, the CAT activity is assayed by ELISA. The fixed concentration of CD2809 used is $5 \times 10^{-8}$M and corresponds to its $EC_{50}$.

The subject of the present invention is also, as medicaments, the compounds of formula (I) as defined above.

The compounds according to the invention are particularly suitable in the following fields of treatment:

1) for treating dermatological complaints associated with a keratinization disorder which has a bearing on differentiation and on proliferation, in particular for treating common acne, comedones, polymorphonuclear leukocytes, acne rosacea, nodulocystic acne, acne conglobata, senile acne and secondary acne such as solar acne, medication-induced acne or occupational acne, 2) for treating other types of keratinization disorders, in particular ichthyosis, ichthyosiform states, Darrier's disease, palmoplantar keratoderma, leucoplasias and leucoplasiform states, and cutaneous or mucous (buccal) lichen, 3) for treating other dermatological complaints associated with a keratinization disorder having an inflammatory and/or immunoallergic component and, in particular, all forms of psoriasis, whether it is cutaneous, mucous or ungual psoriasis, and even psoriatic rheumatism, or alternatively cutaneous atopy, such as eczema, or respiratory atopy or alternatively gingival hypertrophy; the compounds may also be used in certain inflammatory complaints which do not exhibit a keratinization disorder, 4) for treating all dermal or epidermal proliferations, whether benign or malignant and whether or not they are of viral origin, such as common warts, flat warts and verruciform epidermodysplasia, it being possible for the oral or florid papillomatoses and the proliferations to be induced by ultraviolet radiation, in particular in the case of basocellular and spinocellular epitheliomas, 5) for treating other dermatological disorders such as bullosis and collagen diseases, 6) for treating certain ophthalmological disorders, in particular corneopathies, 7) for repairing or combating both light-induced and chronological ageing of the skin or for reducing actinic keratoses and pigmentations, or any pathology associated with chronological or actinic ageing, 8) for preventing or curing the stigmata of epidermal and/or dermal atrophy induced by local or systemic corticosteroids, or any other form of skin atrophy, 9) for preventing or treating cicatrization disorders, for preventing or repairing stretchmarks, or for encouraging cicatrization, 10) for combating disorders of sebaceous functioning such as the hyperseborrhoea of acne or simple seborrhoea, 11) in the treatment or prevention of cancerous or precancerous states, 12) in the treatment of inflammatory complaints such as arthritis, 13) in the treatment of any complaint of viral origin on the skin or generally, 14) in the prevention or treatment of alopecia, 15) in the treatment of dermatological or general complaints having an immunological component, 16) in the treatment of complaints of the cardiovascular system such as arteriosclerosis or hypertension and noninsulin-dependent diabetes, 17) in the treatment of skin disorders due to exposure to UV radiation.

In the therapeutic fields mentioned above, the compounds according to the invention may advantageously be employed in combination with other compounds having retinoid-type activity, with D vitamins or derivatives thereof, with corticosteroids, with anti-free-radical agents, α-hydroxy or a-keto acids or derivatives thereof, or alternatively with ion-channel blockers. The term D vitamins or derivatives thereof is understood to refer, for example, to vitamin $D_2$ or $D_3$ derivatives and in particular 1,25-dihydroxy vitamin $D_3$. The term anti-free-radical agent is understood to refer, for example, to α-tocopherol, superoxide dismutase, ubiquinol or certain metal-chelating agents. The term α-hydroxy or α-keto acids or derivatives thereof is understood to refer, for example, to lactic acid, malic acid, citric acid, glycolic acid, mandelic acid, tartaric acid, glyceric acid or ascorbic acid or salts, amides or esters thereof. Lastly, the term ion-channel blockers is understood to refer, for example, to Minoxidil (2,4-diamino-6-piperidinopyrimidine 3-oxide) and derivatives thereof.

The subject of the present invention is also medicinal compositions containing at least one compound of formula (I) as defined above, one of the optical or geometrical isomers thereof or one of the salts thereof.

The subject of the present invention is thus a novel medicinal composition intended in particular for treating the abovementioned complaints, and which is characterized in that it comprises, in a pharmaceutically acceptable support which is compatible with the mode of administration selected for this composition, at least one compound of formula (I), one of the optical or geometric isomers thereof or one of the salts thereof.

The compounds according to the invention may be administered enterally, parenterally, topically or ocularly.

Via the enteral route, the medicinal products may be in the form of tablets, gelatin capsules, sugar-coated tablets, syrups, suspensions, solutions, powders, granules, emulsions, microspheres or nanospheres or polymeric or lipid vesicles which allow controlled release. Via the parenteral route, the compositions may be in the form of solutions or suspensions for infusion or for injection.

The compounds according to the invention are generally administered at a daily dose of about 0.01 mg/kg to 100 mg/kg of body weight, taken in 1 to 3 doses.

Via the topical route, the pharmaceutical compositions based on compounds according to the invention are more particularly intended for treating the skin and mucous membranes and may, in this case, be in the form of ointments, creams, milks, salves, powders, impregnated pads, solutions, gels, sprays, lotions or suspensions. They may also be in the form of microspheres or nanospheres or polymeric or lipid vesicles or polymeric patches and hydrogels which allow controlled release. These topical-route compositions may moreover be either in anhydrous form or in an aqueous form, depending on the clinical indication.

Via the ocular route, they are mainly eyedrops.

These compositions for topical or ocular use contain at least one compound of formula (I) as defined above, or one of the optical or geometric isomers thereof, or alternatively one of the salts thereof, at a concentration preferably of between 0.001% and 5% by weight relative to the total weight of the composition.

The compounds of formula (I) according to the invention also find an application in the cosmetic field, in particular in body and hair hygiene and especially for treating skin with a tendency towards acne, for promoting the regrowth of the hair, for combating hair loss, for controlling the greasy appearance of the skin or the hair, in protection against the harmful effects of sunlight or in the treatment of physiologically dry skin, and for preventing and/or combating light-induced or chronological ageing.

In the cosmetic field, the compounds according to the invention may also advantageously be employed in combination with other compounds having retinoid-type activity, with D vitamins or derivatives thereof, with corticosteroids, with anti-free-radical agents, α-hydroxy or α-keto acids or derivatives thereof, or alternatively with ion-channel blockers, all of these different products being as defined above.

The present invention is thus also directed towards a cosmetic composition which is characterized in that it comprises, in a cosmetically acceptable support which is suitable for topical application, at least one compound of formula (I) as defined above, or one of the optical or geometric isomers thereof or one of the salts thereof, it being possible for this cosmetic composition to be, in particular, in the form of a cream, a milk, a lotion, a gel, microspheres or nanospheres or polymeric or lipid vesicles, a soap or a shampoo.

The concentration of compound of formula (I) in the cosmetic compositions according to the invention is advantageously between 0.001% and 3% by weight relative to the composition as a whole.

The medicinal and cosmetic compositions according to the invention may also contain inert additives or even pharmacodynamically or cosmetically active additives or combinations of these additives and, in particular, wetting agents; depigmenting agents such as hydroquinone, azelaic acid, caffeic acid or kojic acid; emollients; moisturizing agents such as glycerol, PEG 400, thiamorpholinone and derivatives thereof, or, alternatively, urea; anti-seborrhoea or anti-acne agents such as S-carboxymethylcysteine, S-benzylcysteamine, the salts and the derivatives thereof, or benzoyl peroxide; antibiotics such as erythromycin and esters thereof, neomycin, clindamycin and esters thereof, and tetracyclines; antifungal agents such as ketoconazole or 4,5-polymethylene-3-isothiazolidones; agents for promoting the regrowth of the hair, such as Minoxidil (2,4-diamino-6-piperidinopyrimidine 3-oxide) and derivatives thereof, Diazoxide (7-chloro-3-methyl-1,2,4-benzothiadiazine 1,1-dioxide) and Phenytoin (5,5-diphenylimidazolidine-2,4-dione); non-steroidal anti-inflammatory agents; carotenoids and, in particular, β-carotene; anti-psoriatic agents such as anthraline and derivatives thereof and, lastly, eicosa-5,8,11,14-tetraynoic acid and eicosa-5,8,11-trynoic acid, the esters and the amides thereof.

The compositions according to the invention may also contain flavour-enhancing agents, preserving agents such as para-hydroxybenzoic acid esters, stabilizing agents, moisture regulators, pH regulators, osmotic pressure modifiers, emulsifying agents, UV-A and UV-B screening agents, and antioxidants such as a-tocopherol, butylhydroxyanisole or butylhydroxytoluene.

Several examples for obtaining active compounds of formula (I) according to the invention, as well as various concrete formulations based on such compounds, will now be given by way of illustration and with no limiting nature.

EXAMPLE 1

3-[3-(5,5,8,8-Tetramethyl-5,6,7,8-tetrahydro-2-naphthylcarbonyl)phenyl]accrylic acid.

(a) 3-Iodobenzoyl chloride.

A solution of 15 g (0.06 mol) of 3-iodobenzoic acid in 100 ml of anhydrous dichloromethane is introduced into a round-bottomed flask, 13 ml (0.063 mol) of dicyclohexylamine are added and the mixture is stirred for one hour. 4.6 ml (0.063 mol) of thionyl chloride are then added and the mixture is stirred for one hour. The mixture is evaporated to dryness, the residue is taken up in anhydrous ethyl ether, the dicyclohexylamine salt is filtered off and the filtrate is evaporated. 17 g (100%) of the crude acid chloride are collected, which product will be used without further purification for the rest of the synthesis.

(b) 3-Iodophenyl-(5,5,8,8-tetramethyl-5,6,7,8-tetrahydro-2-naphthyl)methanone.

10.3 g (55 mmol) of 5,5,8,8-tetramethyl-5,6,7,8-tetrahydro-2-naphthalene, 8.1 g (60.5 mmol) of aluminium chloride and 100 ml of dichloromethane are introduced into a three-necked flask under a stream of nitrogen. A solution of 16.1 g (65 mmol) of 3-iodobenzoyl chloride, prepared above, in 50 ml of dichloromethane is introduced dropwise, at 0° C., and the mixture is allowed to return to room temperature. The reaction medium is poured into water, the mixture is extracted with dichloromethane and the organic phase is separated out after settling has taken place, dried over magnesium sulphate and evaporated. The residue obtained is purified by chromatography on a column of silica eluted with a mixture of dichloromethane and heptane (50/50). After evaporation of the solvents, 12.5 g (54.6%) of the expected keto derivative with a melting point of 130–1° C. are collected.

(c) Methyl 3-[3-(5,5,8,8-tetramethyl-5,6,7,8-tetrahydro-2-naphthylcarbonyl)phenyl]acrylate.

A solution of 2 g (4.8 mmol) of 3-iodophenyl-(5,5,8,8-tetramethyl-5,6,7,8-tetrahydro-2-naphthyl)-methanone in 30 ml of DMF is introduced into a three-necked flask under a stream of nitrogen, followed by successive addition of 1.7 g of potassium carbonate, 1.4 g of tetrabutylammonium chloride and 600 μl (6.2 mmol) of methyl acrylate. The reaction medium is degassed by bubbling a stream of argon through it, and 22 mg (0.1 mmol) of palladium acetate are introduced. The reaction medium is heated at 55° C. for six hours and then poured into water, the mixture is extracted with ethyl acetate and the organic phase is separated out after settling has taken place, washed with water, dried over magnesium sulphate and evaporated. The residue obtained is purified by chromatography on a column of silica eluted with a mixture of ethyl acetate and heptane (90/10). After evaporation of the solvents, 1.39 g (77%) of the expected methyl ester, with a melting point of 103–4° C., are collected.

(d) 3-[3-(5,5,8,8-Tetramethyl-5,6,7,8-tetrahydro-2-naphthylcarbonyl)phenyl]acrylic acid.

A solution of 1.8 g (4.8 mmol) of the above methyl ester in 20 ml of THF is introduced into a round-bottomed flask and 20 ml of 2N sodium hydroxide solution are added. The reaction medium is stirred at room temperature for six hours and evaporated to dryness. The residue is taken up in water, the mixture is acidified to pH 1 with hydrochloric acid and extracted with ethyl ether, and the organic phase is separated out after settling has taken place, washed with water, dried over magnesium sulphate and evaporated. The residue is triturated in heptane, filtered off and dried. 1.5 g (86%) of 3-[3-(5,5,8,8-tetramethyl-5,6,7,8-tetrahydro-2-naphthylcarbonyl)-phenyl]acrylic acid, with a melting point of 160–5° C., are collected.

EXAMPLE 2

3-[3-(3,5,5,8,8-Pentamethyl-5,6, 7,8-tetrahydro-2-naphthylcarbonyl)phenyl]acrylic acid.

(a) 3-Iodophenyl-(3,5,5,8,8-pentamethyl-5,6,7,8-tetrahydro-2-naphthyl)methanone.

In a similar manner to that of Example 1(b), by reaction of 11.8 g (58 mmol) of 3,5,5,8,8-pentamethyl-5,6,7,8-tetrahydro-2-naphthalene with 18.7 g (68 mmol) of 3-iodobenzoyl chloride, 6.5 g (82%) of the expected keto derivative are obtained in the form of a yellowish oil.

(b) Methyl 3-[3-(3,5,5,8,8-pentamethyl-5,6,7,8-tetrahydro-2-naphthylcarbonyl)phenyl]acrylate.

In a manner similar to that of Example 1(c) by reaction of 6.54 g (15 mmol) of 3-iodophenyl-(3,5,5,8,8-pentamethyl-5,6,7,8-tetrahydro-2-naphthyl)-methanone with 1.8 ml (19.7 mmol) of methyl acrylate, 6.5 g (100%) of the expected methyl ester are obtained in the form of an orange-coloured oil.

(c) 3-[3-(3,5,5,8,8-Pentamethyl-5,6,7,8-tetrahydro-2-naphthylcarbonyl)phenyl]acrylic acid.

In a manner similar to that of Example 1 (d), starting with 6.5 g (15 mmol) of the above methyl ester, 2.1 g (38%) of 3-[3-(3,5,5,8,8-pentamethyl- 5,6,7,8-tetrahydro-2-naphthylcarbonyl)phenyl]acrylic acid, with a melting point of 176–7° C., are obtained.

EXAMPLE 3

3-[3-(5,5,8, 8-Tetramethyl-5, 6,7, 8-tetrahydro-2-naphthylthio)phenyl]acrylic acid.

1.26 g (5.7 mmol) of 5,6,7,8-tetrahydro-5,5,8,8-tetramethyl-2-naphthylthiol, 1.3 g (5.7 nmol) of 3-bromocinnamic acid and 100 ml of tert-butyl alcohol are introduced into a three-necked flask under a stream of nitrogen. 2.3 g (20 mmol) of potassium tert-butoxide and then 200 mg of tetrakis(triphenyl-phosphine)palladium(0) are introduced portionwise, followed by refluxing for eight hours. The reaction medium is poured into water, the pH is adjusted to 5 with 1N hydrochloric acid, the mixture is extracted with ethyl acetate and the extracts are dried over magnesium sulphate and evaporated. The residue obtained is purified by chromatography on a column of silica eluted with a mixture of ethyl acetate and heptane (50/50). After evaporation of the solvents, 610 mg (29%) of 3-[3-(5,5,8,8-tetramethyl-5,6,7,8-tetrahydro-2-naphthylthio)phenyl]acrylic acid, with a melting point of 193–4° C., are collected.

EXAMPLE 4

3-[3-(3,5,5,8,8-Pentamethyl-5,6,7,8-tetrahydro-2-naphthylthio)phenyl]acrylic acid.

(a) 3,5,5,8,8-Pentamethyl-5,6,7,8-tetrahydro2-naphthol.

50.8 g (0.27 mol) of 2,5-dichloro-2,5-dimethylhexane, 30 g (0.27 mol) of 2-methylphenol and 500 ml of dichloromethane are introduced into a three-necked flask. 14.8 g (0.11 mol) of aluminium chloride are added portionwise, at 0° C., and the mixture is stirred at room temperature for twelve hours. The reaction medium is poured into ice-cold water, the mixture is extracted with dichloromethane and the organic phase is separated out after settling has taken place, washed with bicarbonate solution, dried over magnesium sulphate and evaporated. The residue obtained is triturated in hexane and filtered off and, after drying, 54.4 g (90%) of the expected phenol, with a melting point of 125–6° C., are collected.

(b) O-3,5,5,8,8-Pentamethyl-5,6,7,8-tetrahydro-2-naphthyl dimethylthiocarbamate.

4.1 g (0.138 mol) of sodium hydride (80% in oil) and 200 ml of DMF are introduced into a round-bottomed flask under a stream of nitrogen. The solution is cooled to 0° C. and a solution of 25.2 g (0.115 mol) of 3,5,5,8,8-pentamethyl-5,6,7,8-tetrahydro-2-naphthol in 100 ml of DMF is added dropwise and stirred until the evolution of gas has ceased, a solution of 18.55 g (0.15 mol) of dimethylthiocarbamoyl chloride in 200 ml of DMF is then added and the mixture is stirred for eight hours at room temperature. The reaction medium is poured into water, the mixture is extracted with ethyl acetate and the organic phase is separated out after settling has taken place, washed with water, dried over magnesium sulphate and evaporated. The solid obtained is purified by chromatography on a column of silica eluted with a mixture of ethyl acetate and hexane (30/70). After evaporation of the solvents, 20 g (68%) of the expected product, with a melting point of 110–1° C., are collected.

(b) S-3,5,5,8,8-Pentamethyl-5,6,7,8-tetrahydro-2-naphthyl dimethylthiocarbamate.

20.1 g (65.8 mmol) of the above product are introduced into a round-bottomed flask under a stream of nitrogen and the mixture is heated at 240° C. for six hours. The reaction medium is extracted with dichloromethane and washed with water, and the organic phase is separated out after settling has taken place, dried over magnesium sulphate and evaporated. 18.1 g (90%) of the expected product, with a melting point of 138–9° C., are collected.

(c) 3,5,5,8,8-Pentamethyl-5,6,7,8-tetrahydro2-naphthylthiol.

23 g (75 -mmol) of the above product and 300 ml of-methyl alcohol are introduced into a roundbottomed flask. 30 g (75 mmol) of sodium hydroxide are added and the mixture is refluxed for three hours. The reaction medium is evaporated and the residue is taken up in water, acidified with concentrated hydrochloric acid and filtered. The solid obtained is washed with water and dried, and 18 g (99%) of 3,5,5,8,8-pentamethyl-5,6,7,8-tetrahydro-2-naphthylthiol, with a melting point of 97–8° C., are collected.

(d) 3-[3-(3,5,5,8,8-Pentamethyl-5,6,7,8-tetrahydro-2-naphthylthio)phenyl]acrylic acid.

5 g (21.4 mmol) of 5,6,7,8-tetrahydro-5,5,8,8-tetramethyl-2-naphthylthiol, 5 g (21.4 mmol) of 3-bromocinnamic acid and 100 ml of tert-butyl alcohol are introduced into a three-necked flask under a stream of nitrogen. 8.4 g (74.8 mmol) of potassium tertbutoxide and then 650 mg of tetrakis(triphenylphosphine)palladium (0) are introduced portionwise, followed by refluxing for eight hours. The reaction medium is poured into water, the pH is adjusted to 5 with 1N hydrochloric acid, this mixture is extracted with ethyl acetate and the extracts are dried over magnesium sulphate and evaporated. The residue obtained is purified by chromatography on a column of silica eluted with a mixture of ethyl acetate and heptane (70/30). After evaporation of the solvents, 5.6 g (69%) of 3-[3-(3,5,5,8,8-pentamethyl-5,6,7,8-tetrahydro-2-naphthyl-thio)phenyl]acrylic acid, with a melting point of 198–9° C., are collected.

EXAMPLE 5

Ethyl 3-{2-[1-(3,5,5,8,8-pentamethyl-5,6,7,8-tetrahydro-2-naphthyl)vinyl]phenyl}acrylate.

(a) 6-[1-(2-Iodophenyl)vinyl]-1,1,4,4,7-pentamethyl-1,2,3,4-tetrahydronaphthalene.

Potassium tert-butoxide (7.26 g, 64.8 mmol) is added to a solution of 2-iodophenyl-(3,5,5,8,8-pentamethyl-5,6,7,8-tetrahydro-2-naphthyl)methanone (20 g, 46.3 mmol) and methyltriphenylphosphonium bromide (21.5 g, 60.2 mmol) in THF (100 ml). The mixture is stirred for 20 h at room temperature. The solution is extracted with ethyl acetate. After separation of the phases by settling, the organic phase is washed twice with 40 ml of water, dried over anhydrous magnesium sulphate and concentrated on a rotary evaporator under vacuum at 40° C. The product is purified by flash chromatography on a column of silica.
White solid. Mass: 17.5 g. Yield: 88%.
NMR d ppm:
1H/CDCl3: 1.23 (s, 6H); 1.27 (s, 6H); 1.66 (s, 4H); 2.30 (s, 3H); 5.48 to 5.53 (dd, 2H); 6.88 to 7.33 (m, 5H) ; 7.89 (d, 1H).
13C/CDCl3: 14.1, CH3/31.9, 4* CH3/ 33.8, 2* Cq/35.2, 2* CH2/98.0, Cq(C−1)/120.3, Cq (C=C)/127.8, CH/ 128.4, CH/128.5, CH/128.8, CH/130.4, CH/132.8, Cq/137.8; Cq/140.1 CH/142.0, Cq/144.2, Cq/146.8, Cq/151.4, Cq.

(b) Methyl 2-[1-(3,5,5,8,8-pentamethyl-5,6,7,8-tetrahydro-2-naphthyl)vinyl]phenylcarboxylate A solution of 6-[1-(2-iodophenyl)vinyl]-1,1,4,4,7-pentamethyl-1,2,3,4-tetrahydronaphthalene (17.2 g, 40 mmol), palladium diacetate (1.02 g, 4.5 mmol) and tributylamine (21.9 ml, 92 mmol) in methanol (500 ml) is heated for 3 h at 100° C. under a pressure of carbon monoxide (3 bar). After concentration on an evaporator under vacuum at 40° C., the oil obtained is diluted in ethyl acetate and washed three times with water. The product is purified by flash chromatography on a column of silica.

Brown solid. Mass: 9.9 g. Yield: 69%. m.p.: 53° C.

1H/CDCl3: 1.22 (s, 6H); 1.26 (s, 6H); 1.65 (s, 4H); 2.06 (s, 3H); 3.49 (s, 3H); 5.38 to 5.48 (dd, 2H); 7.03 (s, 1H); 7.06 (s, 1H); 7.29 to 7.46 (m, 4H); 7.53 to 7.56 (m, 1H).

13C/CDCl3: 20.6, CH3/31.8, 4* CH3/33.8, 2* Cq/35.2, 2* CH2/51.9, CH3/118.0, Cq/127.2, CH/128.4, CH/128.6, CH/128.9, CH/130.2, CH/130.7, CH/131.7, Cq/132.9, Cq/138.0, Cq/141.7, Cq/142.5, Cq/144.1, Cq/149.2, Cq/169.5, Cq.

(c) 2-[1-(3,5,5,8,8-pentamethyl-5,6,7,8-tetrahydro-2-naphthyl)vinyl]phenylcarbaldehyde.

A 1M solution of diisobutylaluminium hydride in toluene (17.3 ml, 17.3 mmol) is added dropwise, at 0° C., to a solution of methyl 2-[1-(3,5,5,8,8-pentamethyl-5,6,7,8-tetrahydro-2-naphthyl)vinyl]phenylcarboxylate (2.5 g, 6.9 mmol) in toluene (50 ml). The solution is stirred for 1 h at 0° C. and then treated with potassium sodium tartrate solution, filtered and taken up in a mixture of ethyl ether and water. The organic phase is washed with water, dried over magnesium sulphate and concentrated on a rotary evaporator under vacuum at 40° C.

The oil obtained is stirred at room temperature for 4 h in the presence of pyridinium dichromate (5 g, 13.3 mmol) in $CH_2Cl_2$ (50 ml), then the solution is filtered through silica and concentrated on a rotary evaporator under vacuum at 40° C. The product is purified by flash chromatography on a column of silica.

White solid. Mass: 1.2 g. Yield: 52%. m.p. =55° C.

1H/CDCl3: 1.26 (s, 6H); 1.28 (s, 6H); 1.68 (s, 4H); 2.18 (s, 3H); 5.30 (d, 1H); 5.71 (d, 1H); 7.05 (s, 1H); 7.16 (s, 1H); 7.22 (dd, 1H); 7.39 (dt, 1H); 7.49 (dt, 1H); 7.96 (dd, 1H); 10.32 (s, 1H).

13C/CDCl3: 20.5, CH3/31.7, 4* CH3/33.8, 2* Cq/34.5, 2* CH2/122.8, CH2/127.5, CH/127.7, CH/128.1, CH/128.7, CH/129.8, CH/132.4, Cq/133.1, CH/134.1, Cq/138.4, Cq/142.5, Cq/144.8, Cq/146.3, Cq/146.4, Cq/192.1, Cq.

(d) Ethyl 3-{2-[1-(3,5,5,8,8-pentamethyl-5,6,7,8-tetrahydro-2-naphthyl)vinyl]phenyl}acrylate.

Sodium hydride at 75% in oil (140 mg, 4.4 mmol) is added to a mixture of 2-[1-(3,5,5,8,8-pentamethyl-5,6,7,8-tetrahydro-2-naphthyl)vinyl]phenylcarbaldehyde (1.2 g, 3.6 mmol) and triethyl phosphonoacetate (1.1 ml, 5.5 mmol) in THF (20 ml). The mixture is stirred for 2 h at room temperature, extracted with ethyl acetate and washed with water. After drying, the organic phase is concentrated on a rotary evaporator under vacuum at 40° C. and the product is purified by flash chromatography on a column of silica.

Mass: 1.28 g. Yield: 88%.

NMR (250 MHz):

1H/CDCl3: 1.13 to 1.33 (m, 15H); 1.67 (s, 4H); 1.97 (s, 3H); 4.21 (q, 2H); 5.27 (d, 1H); 5.60 (s, 1H); 6.3 (d, h); 7.01 (s, 1H); 7.1 to 7.21 (m, 2H); 7.23 to 7.31 (m, 2H); 7.60 (m, 1H); 8.05 (d, 1H).

13C/CDCl3: 14.3, CH3/20.4, CH3/31.8, 4* CH3/33.9, 2* Cq/35.2, 2* CH2/60.3, CH2/118.8, CH/121.4, CH2/127.1, CH/127.4, CH/128.1, CH/128.4, CH/129.4, CH/129.6, CH/132.5, Cq/132.9, Cq/139.0, Cq/142.3, Cq/143.2, Cq/144.2, CH/144.3, Cq/148.1, Cq/166.8, Cq.

EXAMPLE 6

3-{2-[1-(3,5,5,8,8-Pentamethyl-5,6,7,8-tetrahydro-2-naphthyl)vinyl]phenyl}acrylic acid.

A solution of the product of Example 5 (1.28 g, 3.2 mmol) and sodium hydroxide (1.3 g) in THF (50 ml) is refluxed for 6 h, acidified to pH 1 (concentrated HCl), extracted with ethyl acetate and washed with water. After drying, the organic phase is concentrated on a rotary evaporator under vacuum at 40° C. and the product is washed with heptane.

Mass: 880 mg. Yield: 74%. m.p.: 200° C.

1H/CDCl3: 1.26 (s, 12H); 1.67 (s, 4H); 1.93 (s, 3H); 5.29 (d, 1H); 5.61 (d, 1H); 6.28 (d, 1H); 7.01 (s, 1H); 7.18 (s, 1H); 7.20 (m, 1H); 7.25 to 7.35 (m, 2H); 7.61 (m, 1H); 8.12 (d, 1H).

13C/CDCl: 20.4; CH3/31.8; 4* CH3/33.9; 2* Cq/35.2; 2* CH2/117.6; CH/121.4; CH2/127.2; CH/127.5; CH/128.1; CH/128.5; CH/129.7; CH/129.9; CH/132.5; Cq/139.0; Cq/142.4; Cq/143.4; Cq/144.5; Cq/146.6; Cq/148.3; CH/171.9; Cq.

EXAMPLE 7

Ethyl 3-{3-[1-(3,5,5,8,8-pentamethyl-5,6,7,8-tetrahydro-2-naphthyl)vinyl]phenyl}acrylate.

(a) 6-[1-(3-Iodophenyl)vinyl]-1,1,4,4,7-pentamethyl-1,2,3,4-tetrahydronaphthalene.

Potassium tert-butoxide (7.26 g, 64.8 [lacuna]) is added to a solution of 3-iodophenyl-(3,5,5,8,8-pentamethyl-5,6,7,8-tetrahydro-2-naphthyl)-methanone (20 g, 46.3 mmol) and methyltriphenylphosphonium bromide (21.5 g, 60.2 mmol) in THF (100 ml). The mixture is stirred for 20 h at room temperature. The solution is extracted with ethyl acetate. After separation of the phases by settling, the organic phase is washed twice with 40 ml of water, dried over anhydrous magnesium sulphate and concentrated on a rotary evaporator under vacuum at 40° C. The product is purified by flash chromatography on a column of silica.

White solid. Mass: 19.8 g. Yield: 99%. m.p.: 60° C.

NMR d ppm:

1H/CDCl3: 1.26 (s, 6H); 1.29 (s, 6H); 1.69 (s, 4H); 1.96 (s, 3H); 5.22 (d, 1H); 5.68 (s, 1H); 6.98 to 7.29 (m, 6H); 7.58 (dt, 1H); 7.70 (t, 1H).

13C/CDC13: 20.0, CH3/31.9, 4* CH3/33.9, 2* Cq/35.2, 2* CH2/94.5, Cq/116.0, CH/128.2, 2* CH/129.9, CH/132.7, Cq/135.3, CH/136.3, CH/137.8, Cq/142.2, Cq/143.4, Cq/144.3, Cq/148.6, Cq.

(b) Methyl 3-[1-(3,5,5,8,8-pentamethyl-5,6,7,8-tetrahydro-2-naphthyl)vinyl]phenylcarboxylate.

A solution of 6-[1-(3-iodophenyl)vinyl]-1,1,4,4,7-pentamethyl-1,2,3,4-tetrahydronaphthalene (10.8 g, 25 mmol), palladium diacetate (650 mg, 2.9 mmol) and tributylamine (13.8 ml, 58 mmol) in methanol (300 ml) is heated for 3 h at 100° C. under a pressure of carbon monoxide (3 bar). After concentration on an evaporator under vacuum at 40° C., the oil obtained is diluted in ethyl acetate and washed three times with water. The product is purified by flash chromatography on a column of silica.

Brown solid. Mass: 7.7 g. Yield: 86%. m.p.: 75° C.

1H/CDCl3: 1.28 (s, 6H); 1.20 (s, 6H); 1.70 (s, 4H); 1.95 (s, 3H); 3.90 (s, 3H); 5.28 (d, 1H); 5.77 (s, 1H); 7.07 (s, 1H); 7.14 (s, 1H); 7.32 to 7.37 (m, 2H); 7.90 to 7.95 (s, 1H); 8.10 (s, 1H).

13C/CDCl3: 19.8, CH/31.7, 4* CH3/33.7, 2* Cq/35.0, 2* CH2/51.9, CH3/115.8, CH2/127.3, CH/127.9, 2* CH/128.1, CH/128.3, CH/130.0, Cq/131.2, CH/132.5, Cq/137.9, Cq/141.4, Cq/142.1, Cq/144.1, Cq/148.9, Cq/167.0, Cq.

(c) 3-[1-(3,5,5,8,8-Pentamethyl-5,6,7,8-tetrahydro-2-naphthyl)vinyl]phenylcarbaldehyde.

A 1M solution of diisobutylaluminium hydride in toluene (12.5 ml, 12.5 mmol) is added dropwise, at 0° C., to a solution of methyl 3-[1-(3,5,5,8,8-pentamethyl-5,6,7,8-tetrahydro-2-naphthyl)vinyl]phenylcarboxylate (1.8 g, 5 mmol) in toluene (30 ml). The solution is stirred for 1 h at 0° C. and is then treated with potassium sodium tartrate solution, filtered and taken up in a mixture of ethyl ether and water. The organic phase is washed with water, dried over magnesium sulphate and concentrated on a rotary evaporator under vacuum at 40° C.

The oil obtained is stirred at room temperature for 4 h in the presence of pyridinium dichromate (3.6 g, 9.6 mmol) in $CH_2Cl_2$ (50 ml) and the solution is then filtered through silica and concentrated on a rotary evaporator under vacuum at 40° C. The product is purified by flash chromatography on a column of silica.
White solid. Mass: 1.6 g. Yield: 87%. m.p. =62° C.
NMR:
1H/CDCl3: 1.28 (s, 6H); 1.31 (s, 6H); 1.70 (s, 4H); 1.95 (s, 3H); 5.31 (d, 1H); 5.79 (d, 1H); 7.08 (s, 1H); 7.14 (s, 1H); 7.41 to 7.53 (m, 2H); 7.78 (dt, 1H); 7.84 (t, 1H); 10.00 (s, 1H).
13C/CDCl3: 20.3, CH3/32.2, 4* CH3/34.2, 2* Cq/35.5, 2* CH2/116.7, CH2/125.9, CH/128.1, CH/128.36, CH/128.44, CH/128.8, CH/132.9, Cq/138.1, CH/142.5, Cq/142.7, Cq/149.1, Cq/192.8, Cq.

(d) Ethyl 3-{3-[1-(3,5,5,8,8-pentamethyl-5,6,7,8-tetrahydro-2-naphthyl)vinyl]phenyl}acrylate.

Sodium hydride at 75% in oil (183 mg, 5.7 mmol) is added to a mixture of 3-[1-(3,5,5,8,8-pentamethyl-5,6,7,8-tetrahydro-2-naphthyl)vinyl]phenylcarbaldehyde (1.57 g, 4.7 mmol) and triethyl phosphonoacetate (1.44 ml, 7.25 mmol) in THF (30 ml). The mixture is stirred for 1 h at room temperature, extracted with ethyl acetate and washed with water. After drying, the organic phase is concentrated on a rotary evaporator under vacuum at 40° C. and the product is purified by flash chromatography on a column of silica.
Mass: 1.5 g. Yield: 81%.
$^1$H NMR (250 MHz):
1H/CDCl3:–1.28 to 1.31 (m, 15H); 1.70 (s, 4H); 1.95 (s, 3H); 4.25 (q, 2H); 5.25 (d, 1H); 5.73 (d, 1H); 6.41 (d, 1H); 7.07 (s, 1H); 7.13 (s, 1H); 7.25 to 7.45 (m, 4H); 7.64 (d, 1H).
13C/CDCl3: 14.3, CH3/19.9, CH3/31.8, 4* CH3/33.8, Cq/35.2, CH2/60.5, CH2/115.5, CH2/118.2, CH/126.56, CH/126.61, CH/128.0, 2* CH/128.6, CH/128.8, CH/132.6, Cq/134.4, Cq/138.1, Cq/141.8, Cq/142.2, Cq/144.2, Cq/144.7, CH/149.2, Cq/167.0, Cq.

EXAMPLE 8

3-{3-[1-(3,5,5,8,8-Pentamethyl-5,6, 7,8-tetrahydro-2-naphthyl)vinyl]phenyl}acrylic acid.

A solution of the product of Example 7 (1.5 g, 3.7 nmol) and sodium hydroxide (1.5 g) in THF (50 ml) is refluxed for 8 h, acidified to pH 1 (concentrated HCl), extracted with ethyl acetate and washed with water. After drying, the organic phase is concentrated on a rotary evaporator under vacuum at 40° C. and the product is washed with heptane.
Mass: 1.1 g. Yield: 77%. m.p.: 195° C.
1H/CDCl3: 1.28 (s, 6H); 1.3 (s, 6H); 1.70 (s, 4H); 1.96 (s, 3H); 5.27 (d, 1H); 5.74 (d, 1H); 6.41 (d, 1H); 7.08 (s, 1H); 7.14 (s, 1H); 7.31 to 7.49 (m, 4H); 7.75 (d, 1H)
13C/CDCl3: 20.3; CH3/32.2; 4* CH3/34.2; Cq/34.3; Cq/35.5; 2* CH2/116.1; CH2/117.6; CH/127.25; CH/127.3; CH/128.4; 2* CH/129.3; CH/129.5; CH/133.0; Cq/134.4; Cq/138.4; Cq/142.3; Cq/142.6; Cq/144.6; Cq/147.6; CH/149.5; Cq/172.5; Cq.

EXAMPLE 9

Ethyl 3-{2-[1-(5,5,8,8-tetramethyl-5,6,7,8-tetrahydro-2-naphthyl)vinyl]phenyl}acrylate.

(a) 6-[1-(2-Iodophenyl)vinyl]-1,1,4,4-tetramethyl-1,2,3,4-tetrahydronaphthalene.

Potassium tert-butoxide (4.03 g, 36 mmol) is added to a solution of 2-iodophenyl-(3,5,5,8,8-pentamethyl-5,6,7,8-tetrahydro-2-naphthyl)methanone (10.5 g, 25.1 mmol) and methyltriphenylphosphonium bromide (12 g, 33.6 mmol) in THF (50 ml). The mixture is stirred for 4 h at [lacuna] temperature. The solution is extracted with ethyl acetate. After separation of the phases by settling, the organic phase is washed twice with 40 ml of water, dried over anhydrous magnesium sulphate and concentrated on a rotary evaporator under vacuum at 40° C. The product is purified by flash chromatography on a column of silica.
White solid. Mass: 9.54 g. Yield: 91%.

(b) Methyl 2-[1-(5,5,8,8-tetramethyl-5,6,7,8-tetrahydro-2-naphthyl)vinyl]phenylcarboxylate.

A solution of 6-[1-(2-iodophenyl)vinyl]-1,1,4,4-tetramethyl-1,2,3,4-tetrahydronaphthalene (9.5 g, 22 mmol), palladium diacetate (560 mg, 2.5 mmol)-and tributylamine (12 ml, 50 mmol) in methanol (500 ml) is heated for 3 h at 100° C. under a pressure of carbon monoxide (3 bar). After concentration on an evaporator under vacuum at 40° C., the oil obtained is diluted in ethyl acetate and washed three times with water. The product is purified by flash chromatography on a column of silica.
Yellow oil. Mass: 6 g. Yield: 79%.

(c) 2-[1-(5,5,8,8-Tetramethyl-5,6,7,8-tetrahydro2-naphthyl)vinyl]phenylcarbaldehyde.

A 1M solution of diisobutylaluminium hydride in toluene (6.5 ml, 6.5 mmol) is added dropwise, at 0° C., to a solution of methyl 2-[1-(5,5,8,8-tetramethyl-5,6,7,8-tetrahydro-2-naphthyl)vinyl]phenylcarboxylate (1 g, 2.8 mmol) in toluene (30 ml). The solution is stirred for 1 h at 0° C. and then treated with potassium sodium tartrate solution, filtered and taken up in a mixture of ethyl ether and water. The organic phase is washed with water, dried over magnesium sulphate and concentrated on a rotary evaporator under vacuum at 40° C.

The oil obtained is stirred at room temperature for 4 h in the presence of pyridinium dichromate (2 g, 5.3 mmol) in $CH_2Cl_2$ (50 ml) and the solution is then filtered through silica and concentrated on a rotary evaporator under vacuum at 40° C. The product is purified by flash chromatography on a column of silica.
Colourless oil. Mass: 580 mg. Yield: 64%.
$^1$H NMR (CDCl$_3$, 250 MHz):
1H/CDCl3: 1.20 (s, 6H); 1.27 (s, 6H); 1.67 (s, 4H); 5.21 (s, 1H); 5.95 (s, 1H); 7.00 to 7.60 (m, 6H); 8.00 (bd, 1H).

(d) Ethyl 3-{2-[1-(5,5,8,8-tetramethyl-5,6,7,8-tetrahydro-2-naphthyl)vinyl]phenyl}acrylate.

Sodium hydride at 80% in oil (91 mg, 3 mmol) is added to a mixture of 2-[1-(5,5,8,8-tetramethyl-5,6,7,8-tetrahydro-2-naphthyl)vinyl]phenylcarbaldehyde (800 mg, 2.5 mmol) and triethyl phosphonoacetate (600 μl, 3 mmol) in THF (20 ml). The mixture is stirred for 1 h at room temperature, extracted with ethyl acetate and washed with water. After drying, the organic phase is concentrated on a rotary evaporator under vacuum at 40° C. and the product is purified by flash chromatography on a column of silica.
Mass: 800 mg. Yield: 82%.
$^1$NMR (CDCl$_3$, 250 MHz):
1H/CDCl3: 1.20 to 1.28 (m, 15H); 1.66 (s, 4H); 4.16 (q, 1H); 5.12 (s, 1H); 5.86 (s, 1H); 6.32 (d, 1H); 6.99 (bd, 1H); 7.19 to 7.37 (5H); 7.66 (m, 1H); 7.77 (d, 1H).
13C/CDCl3: 14.3, CH3/31.8, 4* CH3/34.1, Cq/34.2, Cq/35.0, CH2/35.1, CH2/60.2, CH2/116.2, CH2/118.9, CH/124.2, CH/125.2, CH/126.4, CH/126.5, CH/127.7, CH/129.5, CH/130.6, CH/133.4, Cq/137.7, CH/143.0, Cq/ 143.6, Cq/144.7, Cq/147.4, Cq/166.8, Cq.

EXAMPLE 10

3-{2-[1-(5,5,8,8-Tetramethyl-5,6,7,8-tetrahydro-2-naphthyl )vinyl]phenyl acrylic acid.

A solution of the product of Example 9 (800 mg, 2.1 mmol) and sodium hydroxide (800 mg) in THF (30 ml) is refluxed for 15 h, acidified to pH 1 (concentrated HCl), extracted with ethyl acetate and washed with water. After drying, the organic phase is concentrated on a rotary evaporator under vacuum at 40° C. and the product is washed with heptane.
Mass: 475 mg. Yield: 64%. m.p.: 135° C.
1H/CDCl3: 1.20 (s, 6H); 1.25 (s, 6H); 1.65 (s, 3H); 5.11 (d, 1H); 5.86 (d, 1H); 6.30 (d, 1H); 6.96 (dd, 1H); 7.19 to 7.39 (m, 5H); 7.67 (m, 1H); 7.86 (d, 1H).
13C/CDCl3: 31.7, 4* CH3/34.1, Cq/34.2, Cq/35.1, 2* CH2/ 117.5, 3* CH/124.3, CH/125.2, CH/126.5, CH/126.6, CH/127.8, CH/130.0, CH/130.6, CH/132.4, Cq/137.6, Cq/143.2, Cq/144.8, Cq/146.0, CH/149.5, Cq/172.2, Cq.

EXAMPLE 11

Ethyl 3 -{3-[1-(5,5,8,8-tetramethyl-5,6,7,8-tetrahydro-2-naphthyl)vinyl]phenyl}acrylate.

(a) Methyl 3-(5,5,8,8-tetramethyl-5,6,7,8-tetrahydro-2-naphthylcarbonyl)benzoate.

A solution of 3-iodophenyl-(5,5,8,8-tetramethyl-5,6,7,8-tetrahydro-2-naphthyl)methanone (10.5 g, 25.1 mmol), palladium diacetate (564 mg, 2.5 mmol) and tributylamine (12 ml, 50.5 mmol) in methanol (500 ml) is heated for 3 h at 100° C. under a pressure of carbon monoxide (3 bar). After concentration on an evaporator under vacuum at 40° C., the oil obtained is diluted in ethyl acetate and washed three times with water. The product is purified by flash chromatography on a column of silica.
White solid. Mass: 6.6 g. Yield: 75%. m.p.: 135° C.

(b) Methyl 3-[1-(5,5,8,8-tetramethyl-5,6,7,8-tetrahydro-2-naphthyl)vinyl]phenylcarboxylate.

Potassium tert-butoxide (3 g, 26.5 mmol) is added to a solution of methyl 3-(5,5,8,8-tetramethyl-5,6,7,8-tetrahydro-2-naphthylcarbonyl)benzoate (6.6 g, 18.9 mmol) and methyltriphenylphosphonium bromide (9.4 g, 26.3 mmol) in THP (60 ml). The mixture is stirred for 1 h at room temperature. The solution is extracted with ethyl acetate. After separation of the phases by settling, the organic phase is washed twice with 40 ml of water, dried over anhydrous magnesium sulphate and concentrated on a rotary evaporator under vacuum at 40° C. The product is purified by flash chromatography on a column of silica.
White solid. Yield: 87%. m.p.: 64° C.

(c) 3-[1-(5,5,8,8-Tetramethyl-5,6,7,8-tetrahydro-2-naphthyl)vinyl]phenylcarbaldehyde.

A 1M solution of diisobutylaluminium hydride in toluene (7.3 ml, 7.3 mmol) is added dropwise, at 0° C., to a solution of methyl 3-[1-(5,5,8,8-tetramethyl-5,6,7,8-tetrahydro-2-naphthyl)vinyl]phenylcarboxylate (1.1 g, 3.16 mmol) in toluene (30 ml). The solution is stirred for 1 h at 0° C. and is then treated with potassium sodium tartrate solution, filtered and taken up in a mixture of ethyl ether and water. The organic phase is washed with water, dried over magnesium sulphate and concentrated on a rotary evaporator under vacuum at 40° C.
The oil obtained is stirred at room temperature for 4 h in the presence of pyridinium dichromate (2.2 g, 5.8 mmol) in CH$_2$Cl$_2$ (50 ml) and the solution is then filtered through silica and concentrated on a rotary evaporator under vacuum at 40° C. The product is purified by flash chromatography on a column of silica.
Yellow oil. Mass: 800 mg. Yield: 80%.
$^1$H NMR/CDCl3: 1.24 (s, 6H); 1.30 (s, 6H); 1.70 (s, 4H); 5.50 (d, 1H); 7.05 (dd, 1H); 7.08 to 7.29 (m, 2H); 7.50 (t, 1H); 7.64 (dt, 1H); 7.83 to 7.89 (m, 2H).

(d) Ethyl 3-{3-[1-(5,5,8,8-tetramethyl-5,6,7,8-tetrahydro-2-naphthyl)vinyl]phenyl}acrylate.

Sodium hydride at 80% in oil (183 mg, 2.3 mmol) is added to a mixture of 3-[1-(5,5,8,8-tetramethyl- 5,6,7,8-tetrahydro-2-naphthyl)vinyl]phenyl-carbaldehyde (50 mg, 1.8 mmol) and triethyl phosphonoacetate (435 μl, 2.2 mmol) in THF (20 ml). The mixture is stirred for 2 h at room temperature, extracted with ethyl acetate and washed with water. After drying, the organic phase is concentrated on a rotary evaporator under vacuum at 40° C. and the product is purified by flash chromatography on a column of silica.
Mass: 690 mg. Yield: 98%.
NMR (250 MHz):
1H/CDCl3: 1.22 to 1.36 (m, 15H); 1.70 (s, 4H); 4.26 (q, 2H); 5.42 (dd, 2H); 6.42 (d, 1H); 7.06 (dd, 1H); 7.24 to 7.52 (m, 6H); 7.68 (d, 1H).
13C/CDCl3: 14.3, CH3/31.8, 4* CH3/34.2, Cq/34.3, Cq/35.07, CH2/35.15, CH2/114.0, CH2/118.4, CH/125.4, CH/126.3, CH/126.4, CH/127.2, CH/128.0, CH/128.6, CH/130.3, CH/134.4, Cq/137.8, Cq/142.5, Cq/144.6, CH/144.8, Cq/149.5, Cq/167.0, Cq.

EXAMPLE 12

3-{3 -[1-(5,5,8,8-Tetramethyl-5,6,7,8-tetrahydro-2-naphthyl)vinyl]phenyl}acrylic acid.

A solution of the product of Example 11 (690 mg, 1.8 mmol) and sodium hydroxide (285 mg) in THF (20 ml) is refluxed for 8 h, acidified to pH 1 (concentrated HCl), extracted with ethyl acetate and washed with water. After drying, the organic phase is concentrated on a rotary evaporator under vacuum at 40° C. and the product is washed with heptane.
Mass: 500 mg. Yield: 78%. m.p.: 140° C.
1H/CDCl3: 1.25 (s, 6H); 1.30 (s, 6H); 1.70 (s, 3H); 5.46 (d, 2H); 6.43 (d, 1H); 7.07 (dd, 1H); 7.28 to 7.54 (m, 6H); 7.77 (d, 1H).
13C/CDCl3: 31.8, 4* CH3/34.2, Cq/34.3, Cq/35.0, CH2/ 35.1, CH2/114.1, CH/117.4, CH/125.3, CH/126.2, CH/126.4, CH/127.4, CH/128.3, CH/128.7, CH/130.8, CH/133.9, CH/137.7, CH/142.5, Cq/144.7, Cq/144.8, Cq/147.1, Cq/149.4, Cq/172.2, Cq.

EXAMPLE 13

Ethyl 3-{3-[1-(5,5,8,8-tetramethyl-5,6, 7,8-tetrahydro-2-naphthyl )ethyl]phenyl}acrylate.

(a) Methyl 3-[1-(5,5,8,8-tetramethyl-5,6,7,8-tetrahydro-2-naphthyl)ethyl]benzoate.

A solution of methyl 3-[1-(5,5,8,8-tetramethyl-5,6,7,8-tetrahydro-2-naphthyl)vinyl]phenylcarboxylate (1.2 g, 3.45 mmol) in ethyl acetate, in the presence of palladium-on-charcoal (0.3 g) at a pressure of 6 bar of hydrogen, is stirred at room temperature for 4 h. The mixture is filtered through Celite and then concentrated on a rotary evaporator under vacuum at 40° C.
Colourless oil. Mass: 1.2 g. Yield: 100%.

(b) 3-[1-(5,5,8,8-Tetramethyl-5,6,7,8-tetrahydro-2-naphthyl)ethyl]carbaldehyde.

Methyl 3-[1-(5,5,8,8-tetramethyl-5,6,7,8-tetrahydro-2-naphthyl)ethyl]benzoate is subjected to a reduction with diisobutylaluminium hydride to give the corresponding alcohol, which is oxidized into the aldehyde by the action of pyridinium dichromate according to the process described in Example 5(c).
Yellow oil. Mass: 1.1 g. Yield: 100%.
b 1H/CDCl3: 1.25 (bs, 12H); 1.66 (bs, 7H); 4.17 (q, 1H); 6.93 (d, 1H); 7.14 to 7.48 (m, 4H); 7.69 (bd, 1H); 7.78 (s, 1H).

(c) Ethyl 3-{3-[1-(5,5,8,8-tetramethyl-5,6,7,8-tetrahydro-2-naphthyl)ethyl]}acrylate.

Ethyl 3-{3-[1-(5,5,8,8-tetramethyl-5,6,7,8-tetrahydro-2-naphthyl)ethyl]}acrylate is formed by the action of triethyl phosphonoacetate on 3-[1-(5,5,8,8-tetramethyl-5,6,7,8-tetrahydro-2-naphthyl)ethyl]-carbaldehyde according to the process described in Example 5(d).
Colourless oil. Mass: 1.25 g. Yield: 93%.
1H/CDCl3: 1.25 to 1.36 (m, 15H); 1.61 to 1.66 (m, 7H); 4.09 (q, 1H); 4.26 (q, 2H); 6.40 (d, 1H); 6.92 (dd, 1H); 7.14 to 7.38 (m, 7H); 7.65 (d, 1H).
13C/CDCl3: 14.4; CH3/31.96; 4* CH3/34.0; Cq/34.3; Cq/35.3; CH2/44.5; CH3/60.5; CH2/118.1; CH/124.8; CH/125.6; 2* CH/126.6; CH/127.6; CH/128.9; CH/129.8; CH/135; Cq/140; Cq/142; Cq/144; Cq/145.0; CH/147; Cq/166; Cq.

EXAMPLE 14

3-{3-[1-(5,5,8,8-Tetramethyl-5,6,7,8-tetrahydro-2-naphthyl)ethyl]phenyl}acrylic acid.

A solution of the product of Example 13 (1.25 g, 3.2 mmol) and sodium hydroxide (1.3 g) in THF (30 ml) is refluxed for 3 h, acidified to pH 1 (concentrated HCl), extracted with ethyl acetate and washed with water. After drying, the organic phase is concentrated on a rotary evaporator under vacuum at 40° C. and the product is washed with heptane.
White solid. Mass: 750 mg. Yield: 65%. m.p.: 145° C.
1H/CDCl3: 1.25 (bs, 12H); 1.61 to 1.66 (m, 7H); 4.11 (q, 1H); 6.42 (d, 1H); 6.93 (dd, 1H); 7.15 to 7.41 (m, 6H); 7.76 (d, 1H).
13C/CDCl3: 21.9, CH3/31.9, 4* CH3/34.0, Cq/34.3, Cq/35.2, 2* CH2/44.5, CH/116.8, CH/124.7, CH/125.5, CH/125.9, CH/126.5, CH/127.9, CH/128.9, CH/130.3, CH/134.0, Cq/142.3, Cq/142.7, Cq/144.8, Cq/147.4, CH/147.6, Cq/171.3, Cq.

EXAMPLE 15

Ethyl 3-{2-[1-(5,5,8,8-tetramethyl-5,6,7,8-tetrahydro-2-naphthyl)ethyl]phenyl}acrylate.

(a) Methyl 2-[1-(5,5,8,8-tetramethyl-5,6,7,B-tetrahydro-2-naphthyl)ethyl]benzoate.

A solution of methyl 2-[1-(5,5,8,8-tetramethyl- 5,6,7,8-tetrahydro-2-naphthyl)vinyl]phenylcarboxylate (1.1 g, 3.–48 mmol) in ethyl acetate, in the presence of palladium-on-charcoal (275 mg) at a pressure of 6 bar of hydrogen, is stirred at room temperature for 4 h. The mixture is filtered through Celite and then concentrated on a rotary evaporator under vacuum at 40° C.
Colourless oil. Mass: 1.1 g. Yield: 100%.

(b) 2-[1-(5,5,8,8-Tetramethyl-5,6,7,8-tetrahydro-2-naphthyl)ethyl]carbaldehyde.

Methyl 2-[1-(5,5,8,8-tetramethyl-5,6,7,8-tetrahydro-2-naphthyl)ethyl]benzoate is subjected to a reduction with diisobutylaluminium hydride to give the corresponding alcohol, which is oxidized into the aldehyde by the action of pyridinium dichromate according to the process described in Example 5(c).
Colourless oil. Mass: 1.1 g. Yield: 100%.
1H/CDCl3: 1.20 to 1.30 (m, 12H); 1.58 to 1.74 (m, 7H); 5.13 (q, 1H); 6.91 (dd, 1H); 7.13 to 7.56 (6H); 7.82 (dd, 1H); 10.35 (s, 1H).

(c) Ethyl 3-{2-[1-(5,5,8,8-tetramethyl-5,6,7,8-tetrahydro-2-naphthyl)ethyl]}acrylate.

Ethyl 3-{2-[1-(5,5,8,8-tetramethyl-5,6,7,8-tetrahydro-2-naphthyl)ethyl]}acrylate is formed by the action of triethyl phosphonoacetate on 3-[1-(5,5,8,8-tetramethyl-5,6,7,8-tetrahydro-2-naphthyl)ethyl]-carbaldehyde according to the process described in Example 5(d).

Colourless oil Mass: 450 mg. Yield: 33%.
1H/CDCl3: 1.21 to 1.35 (m, 15H); 1.56 to 1.65 (m, 7H); 4.25 (q, 2H); 4.48 (q, 1H); 6.26 (d, 1H); 6.90 (dd, 1H); 7.14 to 7.37 (m, 5H); 7.49 (d, 1H); 8.14 (d, 1H)
13C/CDCl3: 14.3, CH3/22.0; CH3/31.8; 4* CH3/33.9; Cq/34.2; Cq/35.1; CH2/35.2; CH2/40.2; CH/60.4; CH2/120.2; CH/124.8; CH/125.7; CH/126.3; CH/126.5; CH/126.8; CH/127.4; CH/130.0; CH/133.3; Cq/142.0; Cq/142.4; Cq/142.8; CH/144.7; Cq/145.8; Cq/166.9; Cq.

EXAMPLE 16

3-{2-[1-(5,5,8,8-tetramethyl-5,6,7,8-tetrahydro-2-naphthyl)ethyl]phenyl}acrylic acid.

A solution of the product of Example 15 (450 mg, 1.1 mmol) and sodium hydroxide (450 mg) in THF (20 ml) is refluxed for 15 h, acidified to pH 1 (concentrated HCl), extracted with ethyl acetate and washed with water.-After drying, the organic phase is concentrated on a rotary evaporator under vacuum at 40° C. and the product is washed with heptane.
White solid. Mass: 325 mg. Yield: 79%. m.p.: 150° C.
1H/CDCl3: 1.23 to 1.26 (m, 12H); 1.61 to 1.65 (m, 7H); 4.47 (q, 1H); 6.26 (d, 1H); 6.88 (dd, 1H); 7.16 to 7.41 (m, 5H); 7.53 (d, 1H); 8.25 (d, 1H)
13C/CDCl3: 22.0, CH3/31.8, 4* CH3/33.9, Cq/34.2, Cq/35.2, 2* CH2/40.5, CH/100.5, CH/118.8, CH/124.7, CH/ 125.7, CH/126.4, CH/126.5, CH/127.0, CH/127.5, CH/130.4, CH/132.9, Cq/142.0, Cq/142.5, Cq/145.2, 2* Cq/146.0, CH/171.8, Cq.

EXAMPLE 17

Ethyl 3-{2-[1-(3,5,5,8,8-pentamethyl-5,6,7,8-tetrahydro-2-naphthyl)ethyl]phenyl}acrylate.

(a) Methyl 2-[1-(3,5,5,8,8-pentamethyl-5,6,7,8-tetrahydro-2-naphthyl)ethyl]benzoate.

A solution of methyl 2-[1-(3,5,5,8,8-pentamethyl-5,6,7,8-tetrahydro-2-naphthyl)vinyl]phenylcarboxylate (3.5 g, 9.7 mmol) in ethyl acetate, in the presence of palladium-on-charcoal (900 mg) at a pressure of 6 bar of hydrogen, is stirred at room temperature for 4 h. The mixture is filtered through Celite and then concentrated on a rotary evaporator under vacuum at 40° C.

White solid. Mass: 3.44 g. Yield: 98%. m.p.: 48° C.

1H/CDCl3: 1.23 to-1.28 (m, 12H); 1.58 (d, 3H); 1.68 (s, 3H); 1.99 (s, 3H); 3.85 (s, 3H); 5.13 (q, 1H); 6.99 (s, 1H); 7.02 (dd, 1H); 7.19 (dt, 1H); 7.25 (s, 1H); 7.33 (dt, 1H); 7.75 (dd, 1H).

13C/CDCl3: 19.2, CH3/22.0, CH/31.8, 4* CH3/33.7, 2* Cq/35.3, 2* CH2/37.1, CH/51.9, CH3/124.7, CH/125.5, CH/128.2, CH/128.3, CH/129.8, CH/131.8, CH/133.6, Cq/140.5, Cq/141.9, Cq/142.3, Cq/148.0, Cq/168.6, Cq.

(b) 2-[1-(3,5,5,8,8-Pentamethyl-5,6,7,8-tetrahydro-2-naphthyl)ethyl]carbaldehyde.

Methyl 2-[1-(3,5,5,8,8-pentamethyl-5,6,7,8-tetrahydro-2-naphthyl)ethyl]benzoate is subjected to a reduction with diisobutylaluminium hydride to give the corresponding alcohol, which is oxidized into the aldehyde by the action of pyridinium dichromate according to the process described in Example 5(c).

White solid. Mass: 1.6 g. Yield: 53%. m.p.: 135° C.

1H/CDCl3: 1.23 to 1.28 (m, 12H); 1.59 (d, 3H); 1.67 (s, 4H); 2.04 (s, 3H); 5.27 (q, 1H); 7.01 (s, 1H); 7.11 (d, 1H); 7.19 (s, 1H); 7.30 (dt, 1H); 7.46 (dt, 1H); 7.81 (dd, 1H); 10.33 (s, 1H).

13C/CDCl3: 19.7, CH3/22.6, CH3/32.4, 4* CH3/34.3, Cq/34.5, Cq/35.7, 2* CH2/36.2, CH/125.3; CH/126.7, CH/128.8, CH/128.86, CH/132.4, CH/133.45, Cq/133.52, Cq/134.4, CH/140.5, Cq/142.7, Cq/143.1, Cq/149.9, Cq/193.0, CH.

(c) Ethyl 3-{2-[1-(3,5,5,8,8-pentamethyl-5,6,7,8-tetrahydro-2-naphthyl)ethyl]}acrylate.

Ethyl 3-{2-[1-(3,5,5,8,8-pentamethyl-5,6,7,8-tetrahydro-2-naphthyl)ethyl]}acrylate is formed by the action of triethyl phosphonoacetate on 3-[1-(5,5,8,8-tetramethyl-5,6,7,8-tetrahydro-2-naphthyl)ethyl]-carbaldehyde according to the process described in Example 5(d).

Colourless oil. Mass: 1.9 g. Yield: 100%.

1H/CDCl3: 1.23 to 1.33 (m, 15H); 1.51 (d, 3H); 1.66 (s, 4H); 2.09 (s, 3H); 4.25 (q, 2H); 4.52 (q, 1H); 6.3 (d, 1H); 7.00 to 7.013 (m, 2H); 7.18 to 7.30 (m, 3H); 7.48 (dd, 1H); 8.09 (d, 1H).

13C/CDCl3: 13.9, CH3/18.8, CH3/21.3, CH3/31.4, 4* CH3/33.3, Cq/33.6, Cq/34.8, 2* CH2/36.7, CH/60.0, CH2/119.7, CH/124.4, CH/125.8, CH/126.2, CH/126.9, CH/127.8, CH/129.6, CH/132.4, Cq/132.6, Cq/139.6, Cq/141.7, Cq/142.0, Cq/145.5, 2* Cq/166.5, Cq.

EXAMPLE 18

3-{2-[1-(3,5,5,8,8-Pentamethyl-5,6,7,8-tetrahydro-2-naphthyl)ethyl]phenyl}acrylic acid.

A solution of the product of Example 17 (1.9 g, 4.9 mmol) and sodium hydroxide (2 g) in THF (30 ml) is refluxed for 4 h, acidified to pH 1 (concentrated HCl), extracted with ethyl acetate and washed with water. After drying, the organic phase is concentrated on a rotary evaporator under vacuum at 40° C. and the product is washed with heptane.

White solid. Mass: 1.1 g. Yield: 59%. m.p.: 192° C.

1H/CDCl: 1.22 to 1.28 (m, 15H); 1.56 (d, 3H); 1.67 (s, 4H); 2.07 (s, 3H); 4.51 (q, 1H); 6.32 (d, 1H); 7.01 (s, 1H); 7.05 (m, 1H); 7.2 to 7.32 (m, 3H); 7.53 (d, 1H); 8.23 (d, 1H).

13C/CDCl3: 19.4; CH3/22.0; CH3/32.0; 4* CH3/34.0; Cq/34.2; Cq/35.4; 2* CH2/37.4; CH/119.3; CH/125.0; CH/126.5; CH/127.0; CH/127.7; CH/128.5; CH/130.7; CH/ 132.8; Cq/132.8; Cq/140.0; Cq/142.4; Cq/142.7; Cq/145.0; Cq/146.4; CH/172.2; Cq.

EXAMPLE 19

Ethyl 3-{3-[1-(3,5,5,8,8-pentamethyl-5,6,7,8-tetrahydro-2-naphthyl)ethyl]phenyl}acrylate.

(a) Methyl 3-[1-(3,5,5,8,8-pentamethyl-5,6,7,8-tetrahydro-2-naphthyl)ethyl]benzoate.

A solution of methyl 3-[1-(3,5,5,8,8-pentamethyl-5,6,7,8-tetrahydro-2-naphthyl)vinyl]phenylcarboxylate (2.5 g, 6.9 mmol) in ethyl acetate, in the presence of palladium-on-charcoal (700 mg) at a pressure of 6 bar of hydrogen, is stirred at room temperature for 4 h. The mixture is filtered through Celite and then concentrated on a rotary evaporator under vacuum at 40° C.

White solid. Mass: 2.5 g. Yield: 99%. m.p.: 85° C.

1H/CDCl3: 1.22 to 1.29 (m, 15H); 1.62 (d, 3H); 1.62 (s, 4H); 2.14 (s, 3H); 3.89 (s, 3H); 4.27 (q, 1H); 7.02 (s, 1H); 7.23 to 7.43 (m, 3H); 7.83 (dt, 1H); 7.92 (s, 1H).

13C/CDCl3: 19.4, CH3/22.4, CH/31.9, 4* CH3/33.8, 2* Cq/35.2, 2* CH2/41.0, CH/52.0, CH3/124.5, CH/127.1, CH/128.3, CH/129.0, CH/130.0, Cq/132.3, CH/132.9, Cq/139.9, Cq/142.3, Cq/142.6, Cq/147.0, Cq/167.3, Cq.

(b) 3-[1-(3,5,5,8,8-Pentamethyl-5,6,7,8-tetrahydro-2-naphthyl)ethyl]carbaldehyde.

Methyl 3-[1-(3,5,5,8,8-pentamethyl-5,6,7,8-tetrahydro-2-naphthyl)ethyl]benzoate is subjected to a reduction with diisobutylaluminium hydride to give the corresponding alcohol, which is oxidized into the aldehyde by the action of pyridinium dichromate according to the process described in Example 5(c).

Colourless oil. Mass: 2.1 g. Yield: 98%.

1H/CDCl3: 1.23 to 1.29 (m, 15H); 1.60 (d, 3H); 1.67 (s, 4H); 2.14 (s, 3H); 4.64 (q, 1H); 7.03 (s, 1H); 7.21 (s, 1H); 7.39 to 7.45 (m, 2H); 7.66 to 7.71 (m, 2H); 9.97 (s, 1H).

13C/CDCl3: 19.6, CH3/22.4, CH3/32.0, 4* CH3/33.9, Cq/34.2, Cq/35.3, 2* CH2/41.1, CH/124.7, CH/127.6, CH/128.6, CH/129.0, CH/129.1, CH/133.0, Cq/134.1, CH/136.6, Cq/139.8, Cq/142.6, Cq/142.9, Cq/148.0, Cq/192.8, CH.

(c) Ethyl 3-{3-[1-(3,5,5,8,8-pentamethyl-5,6,7,8-tetrahydro-2-naphthyl)ethyl]}acrylate.

Ethyl 3-{3-[1-(3,5,5,8,8-pentamethyl-5,6,7,8-tetrahydro-2-naphthyl)ethyl]}acrylate is formed by the action of triethyl phosphonoacetate on 3-(1-(5,5,8,8-tetramethyl-5,6,7,8-tetrahydro-2-naphthyl)ethyl]-carbaldehyde according to the process described in Example 5(d).

Colourless oil. Mass: 2.5 g. Yield: 96%.

1H/CDCl3: 1.24 to 1.35 (m, 15H); 1.60 (d, 3H); 1.67 (s, 4H); 2.13 (s, 3H); 4.25 (q, 2H); 6.37 (d, 1H); 7.02 (s, 1H); 7.14 to 7.35 (m, 5H); 7.63 (d, 1H)

13C/CDCl3: 14.0, CH3/19.1, CH3/22.0, CH3/31.4, 4* CH3/33.5, Cq/33.7, Cq/34.9, CH2/40.7, CH/60.1, CH2/117.6, CH/124.1, CH/125.0, CH/127.4, CH/128.0, CH/128.5, CH/129.5, CH/132.7, Cq/134.0, Cq/139.6, Cq/142.0, Cq/142.3, Cq/144.6, Cq/147.1, Cq/166.8, Cq.

EXAMPLE 20

3-{3-[1-(3,5,5,8,8-Pentamethyl-5,6,7,8-tetrahydro-2-naphthyl)ethyl]phenyl}acrylic acid.

A solution of the product of Example 19 (2.5 g, 6.4 mmol) and sodium hydroxide (2.5 g) in THF (50 ml) is refluxed for 4 h, acidified to pH 1 (concentrated HCl), extracted with ethyl acetate and washed with water. After drying, the organic phase is concentrated on a rotary evaporator under vacuum at 40° C. and the product is washed with heptane.
White solid. Mass: 435 mg. Yield: 18%. m.p.: 187° C.
1H/CDCl3: 1.26 to 1.29 (m, 12H); 1.61 (d, 3H); 1.67 (s, 4H); 2.14 (s, 3H); 4.24 (q, 1H); 6.39 (d, 1H); 7.03 (s, 1H); 7.17 to 7.38 (m, 5H); 7.74 (d, 1H)
13C/CDCl3: 19.9; CH3/22.8; CH3/32.2; CH3/32.3; 2* CH3/32.55; CH3/34.25; Cq/34.5; Cq/35.7; 2* CH2/41.45; CH/117.3; CH/124.5; CH/126.1; CH/128.4; CH/128.8; CH/129.3; CH/130.7; CH/133.4; Cq/134.4; Cq/ 140.3; Cq/142.8; Cq/143.1; Cq/147.9; Cq/148.0; CH/172.7; Cq.

EXAMPLE 21

Ethyl 3-{2-[1-(5,5,8,8-tetramethyl-5,6,7,8-tetrahydro-2-naphthyl)cyclopropyl]phenyl}acrylate.

(a) Methyl 2-[1-(5,5,8,8-tetramethyl-5,6,7,8-tetrahydro-2-naphthyl)cyclopropyl]benzoate.

Diiodomethane (230 µl, 2.85 mmol) is added dropwise, at 60° C., to a mixture of methyl 2-[1-(5,5,8,8-tetramethyl-5,6,7,8-tetrahydro-2-naphthyl)vinyl]phenylcarboxylate (500 mg, 1.44 mmol) and a 1M solution of diethylzinc in heptane (2.9 ml, 2.9 mmol) in dichloromethane (10 ml). The heating is continued for 4 h. The solution is extracted with ethyl acetate. After separation of the phases by settling, the organic phase is washed with 1N HCl solution and then with water, dried over anhydrous magnesium sulfate and concentrated. The same process is repeated once.
Colourless oil. Mass: 500 mg. Yield: 100%.

(b) 2-[1-(5,5,8,8-Tetramethyl-5,6,7,8-tetrahydro-2-naphthyl)cyclopropyl]carbaldehyde.

Methyl 2-[1-(5,5,8,8-tetramethyl-5,6,7,8-tetrahydro-2-naphthyl)cyclopropyl]benzoate is subjected to a reduction with diisobutylaluminium hydride to give the corresponding alcohol, which is oxidized into the aldehyde by the action of pyridinium dichromate according to the process described in Example 5(c).
Colourless oil. Mass: 990 mg. Yield: 61%.
¹H/CDCl3: 1.13 (s, 6H); 1.21 (s, 6H); 1.42 (t, 2H); 1.48 (t, 2H); 1.62 (s, 4H); 6.69 (dd, 1H); 6.83 (d, 1H); 7.13 (d, 1H); 7.26 (s, 1H); 7.41 (bt, 1H); 7.44 to 7.63 (m, 2H); 7.93 (d, 1H).
13C/CDCl3: 17.8, 2* CH2/26.2, Cq/31.8, 4* CH3/33.8, Cq/34.2, Cq/35.0, 2* CH2/122.8, CH/123.5, CH/126.5, CH/127.4, CH/127.6, CH/131.6, CH/134.1, CH/135.3, Cq/142.3, Cq/142.4, Cq/144.7, Cq/147.6, Cq/192.7, Cq.

(c) Ethyl 3-{2-[1-(5,5,8,8-tetramethyl-5,6,7,8-tetrahydro-2-naphthyl) cyclopropyl]}acrylate.

Ethyl 3-(2 -[1-(5,5,8,8-tetramethyl-5,6,7,8-tetrahydro-2-naphthyl) cyclopropyl]}acrylate is formed by the action of triethyl phosphonoacetate on 2-[1-(5,5,8,8-tetramethyl-5,6,7,8-tetrahydro-2-naphthyl) cyclopropyl] carbaldehyde according to the process described in Example 5(d).
Colourless oil. Mass: 800 mg. Yield: 66%.
1H/CDCl3: 1.15 (s, 6H); 1.21 (s, 6H); 1.27 to 1.32 (m, 7H); 1.61 (s, 4H); 4.22 (q, 1H); 6.28 (d, 1H); 6.81 (dd, 1H); 6.98 (d, 1H); 7.1 1 (d, 1H); 7.26 to 7.39 (m, 2H); 7.55 (t, 2H); 8.30 (d, 1H).
13C/CDCl3: 13.7, CH3/16.3, 2* CH2/27.5, Cq/31.3, 4* CH3/33.4, Cq/33.7, Cq/34.7, 2* CH2/59.8, CH2/118.4, CH/123.5, CH/124.0, CH/125.9, 2* CH/126.7, CH/129.7, CH/131.2, CH/134.6, Cq/141.4, Cq/141.5, Cq/142.8, CH/143.9, Cq/144.2, Cq/166.2, Cq.

EXAMPLE 22

3-{2-[1-(5,5,8, 8-Tetramethyl-5,6,7,8-tetrahydro-2-naphthyl)cyclopropyl]phenyl}acrylic acid.

A solution of the product of Example 21 (800 mg, 2 mmol) and sodium hydroxide (800 mg) in THF (20 ml) is refluxed for 15 h, acidified to pH 1 (concentrated HCl), extracted with ethyl acetate and washed with water. After drying, the organic phase is concentrated on a rotary evaporator under vacuum at 40° C. and the product is washed with heptane.
White solid. Mass: 400 mg. Yield: 54%. m.p.: 200° C.
1H/CDCl3: 1.17 to 1.28 (m, 16H); 1.62 (s, 4H); 6.28 (d, 1H); 6.83 (dd, 1H); 7.01 (d, 1H); 7.12 (d, 1H); 7.28 (t, 1H); 7.39 (t, 1H); 7.58 (m, 2H); 8.45 (d, 1H).
13C/CDCl3: 16.4, 2* CH2/27.8, Cq/31.6, 4* CH3/33.7, Cq/34.1, Cq/35.0, 2* CH2/117.6, CH/123.9, CH/124.3, CH/126.3, CH/126.5, CH/127.0, CH/130.3, CH/131.6, CH/134.6, Cq/141.5, Cq/141.9, Cq/144.4, Cq/144.9, Cq/145.6, CH/172.0, Cq.

EXAMPLE 23

Ethyl 3-{3-[1-(5,5,8,8-tetramethyl-5,6,7,8-tetrahydro-2-naphthyl)cyclopropyl]phenyl}acrylate.

(a) Methyl 3-[1-(5,5,8,8-tetramethyl-5,6,7,8-tetrahydro-2-naphthyl)cyclopropyl]benzoate.

Diiodomethane (1.1 ml, 13.7 mmol) is added dropwise, at 60° C., to a mixture of methyl 3-[1-(5,5,8,8-tetramethyl-5,6,7,8-tetrahydro-2-naphthyl)vinyl]phenylcarboxylate (2.2 g, 6.3 mmol) and a 1M solution of diethylzinc in heptane (13 ml, 13 mmol) in dichloromethane (50 ml). The heating is continued for 15 h. The solution is extracted with ethyl acetate. After separation of the phases by settling, the organic phase is washed with 1N HCl solution and then with water, dried over anhydrous magnesium sulphate and concentrated.
White solid. Mass: 2.3 g. Yield: 100%.

(b) 3-[1-(5,5,8,8-Tetramethyl-5,6,7,8-tetrahydro-2-naphthyl)cyclopropyl]carbaldehyde.

Methyl 3-[1-(5,5,8,8-tetramethyl-5,6,7,8-tetrahydro-2-naphthyl)cyclopropyl]benzoate is subjected to a reduction with diisobutylaluminium hydride to give the corresponding alcohol, which is oxidized into the aldehyde by the action of pyridinium dichromate according to the process described in Example 5(c).
Yellow oil. Mass: 1.1 g. Yield: 52%.
1H/CDCl3: 1.15 to 1.30 (m, 16H); 1.58 (s, 4H); 6.89 (dd, 1H); 7.06 to 7.46 (m, 4H); 7.61 (dt, 1H); 7.68 (s, 1H).
13C/CDCl3: 16.5, 2* CH2/29.5, Cq/31.8, 4* CH3/34.0, Cq/34.3, Cq/35.08, CH2/35.14, CH2/125.7, CH/126.3, CH/126.5, CH/127.4, CH/128.9, CH/129.3, CH/134.9, CH/136.5, Cq/141.5, Cq/142.9, Cq/144.8, Cq/147.4, Cq/192.5, Cq.

(c) Ethyl 3-{3-[1-(5,5,8,8-tetramethyl-5,6,7,8-tetrahydro-2-naphthyl)cyclopropyl]}acrylate.

Ethyl 3-{3-[1-(5,5,8,8-tetramethyl-5,6,7,8-tetrahydro-2-naphthyl)cyclopropyl]}acrylate is formed by the action of triethyl phosphonoacetate on 3-[1-(5,5,8,8-tetramethyl-5,6, 7,8-tetrahydro-2-naphthyl)cyclopropyl]carbaldehyde according to the process described in Example 5(d).
White solid. Mass: 900 mg. Yield: 100%. m.p.: 78° C.
1H/CDCl3: 1.15 to 1.36 (m, 19H); 1.59 (s, 4H); 4.17 (q, 2H); 6.31 (1H); 6.87 (dd, 1H); 7.04 to 7.32 (m, 6H); 7.55 (d, 1H).
13C/CDCl3: 14.2, CH3/16.3, 2* CH2/29.4, 2* CH3/31.7, 2* CH3/33.8, Cq/34.2, Cq/34.99, CH2/35.05, CH2/60.3, CH2/118.0, CH/125.36, CH/125.44, CH/126.0, CH/126.3, CH/128.2, CH/128.6, CH/130.5, CH/134.3, Cq/141.8, Cq/142.5, Cq/144.6, Cq/144.7, CH/146.7, Cq/166.9, Cq.

EXAMPLE 24

3-{3-[1-(5,5,8,8,-Tetramethyl-5,6,7,8-tetrahydro-2-naphthyl)cyclopropyl]phenyl}acrylic acid.

A solution of the product of Example 23 (900 mg, 2.22 mmol) and sodium hydroxide (900 mg) in THF (20 ml) is refluxed for 4 h, acidified to pH 1 (concentrated HCl), extracted with ethyl acetate and washed with water. After drying, the organic phase is concentrated on a rotary evaporator under vacuum at 40° C. and the product is washed with heptane.
White solid. Mass: 450 mg. Yield: 54%. m.p.: 165° C.
1H/CDCl3: 1.27 to 1.35 (m, 16H); 1.66 (s, 4H); 6.41 (d, 1H); 6.95 (dd, 1H); 7.1 (d, 1H); 7.18 (d, 1H); 7.2 to 7.41 (m, 4H); 7.75 (d, 1H).
13C/CDCl3: 16.4 2* CH2/29.5, Cq/31.8, 4* CH3/33.9, Cq/34.3, Cq/35.1, 2* CH2/117.0, CH/125.6, CH/125.8, CH/126.0, CH/126.4, CH/128.6, CH/128.8, CH/131.0, CH/133.9, Cq/141.8, Cq/142.7, Cq/144.7, Cq/147.0, Cq/147.3, CH/171.9, Cq.

EXAMPLE 25

Ethyl 3-{3-[hydroxyamino-(3,5,5,8,8-pentamethyl-5,6,7,8-tetrahydro-2-naphthyl )methyl]phenyl}acrylate.

(a) (3-Iodophenyl)-(3,5,5,8,8-pentamethyl-5,6,7,8-tetrahydro-2-naphthyl)methanone oxime A mixture of 3-iodophenyl-(3,5,5,8,8-pentamethyl-5,6,7,8-tetrahydro-2-naphthyl)methanone (6 g, 13.9 mmol), hydroxylamine hydrochloride (4.8 g, 69.5 mmol) and 4 A molecular sieves in pyridine (17 ml) is refluxed for 8 h. The reaction medium is extracted with ethyl acetate and washed with water. After drying, the organic phase is concentrated on a rotary evaporator under vacuum at 40° C. The two isomers (cis and trans) are separated by flash chromatography on a column of silica.
1st isomer:
White solid. Mass-: 2.98 g. Yield: 48%. m.p.: 58° C.
1H/CDCl3: 1.23 (s, 6H); 1.32 (s, 6H); 1.69 (s, 4H); 2.12 (s, 3H); 6.99 (s, 1H); 7.01 (d, 1H); 7.20 (s, 1H); 7.33 (d, 1H); 7.66 (d, 1H); 7.91 (t, 1H); 7.98 (s, 1H)
13C/CDCl3: 19.5; CH3/32.0; 4* CH3/34.0; Cq/34.3; Cq/35.1; CH2/35.2; CH2/94.5; Cq/126.3; CH/126.6; CH/128.2; CH/129.3; Cq/130.1; CH/132.9; Cq/135.8; CH/138.1; Cq/138.4; CH/142.5; Cq/145.8; Cq/157.4; Cq.
2nd isomer:
White solid. Mass: 720 mg. Yield: 12%. m.p.: 145° C.
1H/CDCl3: 1.23 (s, 6H); 1.32 (s, 6H); 1.69 (s, 4H); 2.12 (s, 3H); 7.07 to 7.08 (m, 1H); 7.13 (d, 1H); 7.18 (s, 1H); 7.42 (d, 1H); 7.70 (d, 1H); 7.9 (s, 1H)
13C/CDCl3: 20.4; CH3/32.0; 4* CH3/34.1; Cq/34.3; Cq/35.2; 2* CH2/93.9; Cq/128.4; CH/129.1; CH/129.2; CH/129.8; CH/133.1; Cq/133.8; Cq/135.4; Cq/138.2; CH/138.6; CH/142.6; Cq/146.2; Cq/156.9; Cq.

(b) Ethyl 3-{3-[hydroxyamino-(3,5,5,8,8-pentamethyl-5,6,7,8-tetrahydro-2-naphthyl)methyl] phenyl}acrylate.

A solution of (3-iodophenyl)-(3,5,5,8,8-pentamethyl-5,6,7,8-tetrahydro-2-naphthyl)methanone oxime (320 mg, 0.7 mmol), palladium diacetate (20 mg, 89 μmol), tributylamine (392 μl, 1.7 mmol) and ethyl acrylate (78 μl, 0.7 mmol) in acetonitrile (10 ml) is heated for 4 h at 80° C. The reaction medium is extracted with ethyl ether and washed with water. After drying, the organic phase is concentrated on a rotary evaporator under vacuum at 40° C. The product is purified by flash- chromatography on a column of silica.
Colourless oil. Mass: 200 mg. Yield: 66%.
1H/CDCl3: 1.15 (s, 6H); 1.20 to 1.33 (m, 9H); 1.50 (s, 4H); 2.06 (s, 3H); 4.16 (q, 2H); 6.30 (d, 1H); 6.95 (s, 1H); 7.14 (s, 1H); 7.17 to 7.59 (m, 5H); 8.84 (bs, 1H)
13C/CDCl3: 14.0; CH3/19.2; CH3/31.6; 4* CH3/33.7; Cq/33.9; Cq/34.8; CH2/34.9; CH2/60.3; CH2/118.5; CH/125.9; CH/126.8; CH/128.1; CH/128.6; CH/128.7; CH/129.2; Cq/132.5; Cq/134.4; Cq/136.5; Cq/142.2; Cq/144.0; CH/145.4; Cq/157.6; Cq/166.7; Cq.

EXAMPLE 26

Ethyl 3-{3-[hydroxyamino-(5,5,8,8-tetramethyl-5,6,7,8-tetrahydro-2-naphthyl) methyl]phenyl acrylate.

The same procedure is used for the other isomer of (3-iodophenyl)-(3,5,5,8,8-pentamethyl-5,6,7,8-tetrahydro-2-naphthyl)methanone oxime.
Yellow solid. Mass: 430 mg. Yield: 46%. m.p. 65° C.
1H/CDCl3: 1.25 to 1.33 (m, 15H); 1.68 (s, 4H); 2.05 (s, 3H); 4.25 (q, 2H); 6.41 (d, 1H); 7.07 (s, 1H); 7.20 (s, 1H); 7.46 to 7.72 (m, 5H).

EXAMPLE 27

3-{3-[Hydroxyamino-(3,5,5,8 8-pentamethyl-5,6,7,8-tetrahydro-2-naphthyl)methyl]phenyl}acrylic acid.

A solution of the product of Example 25 (820 mg, 1.76 mmol) and sodium hydroxide (1 g) in THF (30 ml) is -refluxed for 4 h, acidified to pH 1 (concentrated HCl), extracted with ethyl acetate and washed with water. After drying, the organic phase is concentrated on a rotary evaporator under vacuum at 40° C. and the product is washed with heptane.
White solid. Mass: 643 mg. Yield: 97%. m.p. 185° C.
1H/CDCl3: 1.23 (s, 6H); 1.32 (s, 6H); 1.70 (s, 4H); 2.14 (s, 3H); 6.50 (d, 1H); 7.03 (s, 1H); 7.22 (s, 1H); 7.26 to 7.90 (m, 6H)

EXAMPLE 28

3-{3-[Hydroxyamino-(3,5,5,8,8-pentamethyl-5,6,7,8-tetrahydro-2-naphthyl )methyl]phenyl}acrylic acid.

A solution of the product of Example 26 (430 mg, 0.92 mmol) and sodium hydroxide (500 mg) in THF (20 ml) is refluxed for 4 h, acidified to pH 1 (concentrated HCl), extracted with ethyl acetate and washed with water. After drying, the organic phase is concentrated on a rotary evaporator under vacuum at 40° C. and the product is washed with heptane.
White solid. Mass: 340 mg. Yield: 98%. m.p.: 132° C.

1H/CDCl3: 1.18 (s, 6H); 1.22 (s, 6H); 1.62 (s, 4H); 1.96 (s, 3H); 6.32 (d, 1H); 6.99 (s, 1H); 7.14 (s, 1H); 7.30 to 7.65 (m, 5H).

EXAMPLE 29

Ethyl 3-{3-[2-(3,5,5, 8,8-pentamethyl-5,6, 7,8-tetrahydro-2-naphthyl)-[1,3]-dithian-2-yl]phenyl}acrylate.

(a) 2-(3-Iodophenyl)-2-(3,5,5,8,8-pentamethyl-5,6,7, 8-tetrahydro-2-naphthyl)-[1,3]-dithiane.

A mixture of 3-iodophenyl-(3,5,5,8,8-pentamethyl-5,6,7, 8-tetrahydro-2-naphthyl)methanone (2 g, 4.6 mmol), trifluoroetherate diethyl etherate (3.6 mmol) and propanedithiol (0.5 ml, 5.1 mmol) in dichloromethane (50 ml) is stirred at room temperature for 24 h. The reaction medium is extracted with ethyl ether and washed with water. After drying, the organic phase is concentrated on a rotary evaporator under vacuum at 40° C. The product is purified by flash chromatography on a column of silica.

White solid. Mass: 1.54 g. Yield: 65%.

1H/CDCl3: 1.26 (s, 12H): 1.68 (s, 4H); 1.90 to 2.04 (m, 2H); 2.08 (s, 3H); 2.75 to 2.97 (m, 4H); 6.99 (s, 1H); 7.03 (d, 1H); 7.42 (d, 1H); 7.58 (d, 1H); 7.73 (s, 1H), 8.09 (t, 1H)

13C/CDCl3: 22.5; CH3/24.2; CH2/29.5; 2* CH2/31.8; 4* CH3/33.8; 2* Cq/35.1; 2* Cq/2/94.2; Cq/128.0; CH/129.0; CH/129.9; CH/131.2; CH/134.0; Cq/136.4; CH/137.4; CH/141.3; Cq/144.1; Cq/146.1; Cq (b) Ethyl 3-{3-[2-(3,5,5,8,8-pentamethyl-5,6,7,8-tetrahydro-2-naphthyl)-[1,3]-dithian-2-yl]phenyl)acrylate.

Ethyl 3-{3-[2-(3,5,5,8,8-pentamethyl-5,6,7,8-tetrahydro-2-naphthyl)-[1,3]-dithian-2-yl]phenyl}-acrylate is formed from 2-(3-iodophenyl)-2-(5,5,8,8-tetramethyl-5,6,7,8-tetrahydro-2-naphthyl)-[1,3]-dithiane according to the process described in Example 25 b.

Brown solid. Mass: 770 mg. Yield: 68%.

1H/CDCl3: 1.23 to 1.32 (m, 15H); 1.63 (s, 4H); 1.96 to 2.02 (m, 2H); 2.04 (s, 3H); 2.76 to 2.98 (m, 4H); 2.24 (q, 2H); 6.42 (d, 1H); 6.99 (s, 1H); 7.27 (d, 1H); 7.32 (d, 1H); 7.43 (d, 1H); 7.53 (d, 1H); 7.65 (d, 1H); 7.81 (s, 1H); 7.84 (bs, 1H)

13C/CDCl3: 14.3; CH3/22.4; CH3/24.3; CH2/29.6; 2* CH2/31.7; 4* CH3/33.7; Cq/33.0; Cq/35.1; 2* CH2/60.4; CH2/61.6; Cq/118.3; CH/126.6; CH/128.6; CH/128.8; CH/129.1; CH/130.5; CH/131.2; CH/134.0; Cq/134.4; Cq/136.5; Cq/141.2; Cq/144.0; Cq/144.6; CH+Cq/167.0; Cq

EXAMPLE 30

3-{3-[2-(3,5,5,8,8 -Pentamethyl -5,6, 7,8-tetrahydro-2-naphthyl)-[1,3]-dithian-2-yl]phenyl}acrylic acid.

In a similar manner to that of Example 1d), starting with 960 mg (1.9 mmol) of ethyl 3-{3-[2-(5,5,8,8-pentamethyl-5,6,7,8-tetrahydro-2-naphthyl)-[1,3-dithian-2-yl]phenyl}acrylate, 770 mg (68%) of 3-{3-[2-(5,5,8,8-pentamethyl-5,6,7,8-tetrahydro-2-naphthyl)-[1,3]-dithian-2-yl]phenyl}acrylic acid are obtained.

Yellow solid. Mass: 750 mg. Yield: 83%.

1H/CDCl3: 1.26 (s, 6H); 1.33 (s, 6H); 1.66 (s, 2H); 1.89 (m, 2H); 2.31 (s, 3H); 2.80 (4H); 7.05 to 7.16 (m, 2H); 7.49 (bt, 2H); 7.94 (d, 1H); 8.09 (s, 1H); 8.28 (s, 1H).

EXAMPLE 31

Examples of Formulations p0 1) ORAL ROUTE (a) The following composition is prepared in the form of a 0.8 g tablet

| | |
|---|---|
| Compound of Example 3 | 0.005 g |
| Pregelatinized starch | 0.265 g |
| Microcrystalline cellulose | 0.300 g |
| Lactose | 0.200 g |
| Magnesium stearate | 0.030 g |

(b) A drinkable suspension intended to be packaged in 5 ml ampules is prepared

| | |
|---|---|
| Compound of Example 1 | 0.050 g |
| Glycerol | 0.500 g |
| 70% sorbitol | 0.500 g |
| Sodium saccharinate | 0.010 g |
| Methyl para-hydroxybenzoate | 0.040 g |
| Flavouring qs | |
| Purified water qs | 5 ml |

(c) The following formulation intended to be packaged in gelatin capsules is prepared:

| | |
|---|---|
| Compound of Example 2 | 0.025 g |
| Corn starch | 0.060 g |
| Lactose qs | 0.300 g |

The gelatin capsules used consist of gelatin, titanium oxide and a preserving agent.

2) TOPICAL ROUTE (a) The following nonionic water-in-oil cream is prepared:

| | |
|---|---|
| Compound of Example 4 | 0.100 g |
| Mixture of emulsifying lanolin alcohols, waxes and refined oils, sold by the company BDF under the name "Anhydrous Eucerin" | 39.900 g |
| Methyl para-hydroxybenzoate | 0.075 g |
| Propyl para-hydroxybenzoate | 0.075 g |
| Sterile demineralized water qs | 100.000 g |

(b) A gel is prepared by making the following formulation:

| | |
|---|---|
| Compound of Example 6 | 0.050 g |
| Base erythromycin | 4.000 g |
| Butyl hydroxytoluene | 0.050 g |
| Hydroxypropylcellulose sold by the company Hercules under the name "Klucel HF" | 2.000 g |
| Ethanol (at 95°) qs | 100.000 g |

(c) An anti-seborrhoeic lotion is prepared by mixing together the following ingredients:

| | |
|---|---|
| Compound of Example 5 | 1.000 g |
| Propylene glycol | 5.000 g |
| Butyl hydroxytoluene | 0.100 g |
| Ethanol (at 95°) qs | 100.000 g |

(d) A cosmetic composition to combat the harmful effects of sunlight is prepared by mixing together the following ingredients:

| | |
|---|---|
| Compound of Example 8 | 1.000 g |
| Benzylidenecamphor | 4.000 g |
| Fatty acid triglycerides | 31.000 g |
| Glyceryl monostearate | 6.000 g |
| Stearic acid | 2.000 g |
| Cetyl alcohol | 1.200 g |
| Lanolin | 4.000 g |
| Preserving agents | 0.300 g |
| Propylene glycol | 2.000 g |
| Triethanolamine | 0.500 g |
| Fragrance | 0.400 g |
| Demineralized water qs | 100.000 g |

(e) The following nonionic oil-in-water cream is prepared:

| | |
|---|---|
| Compound of Example 7 | 0.500 g |
| Vitamin D3 | 0.020 g |
| Cetyl alcohol | 4.000 g |
| Glyceryl monostearate | 2.500 g |
| PEG-50 stearate | 2.500 g |
| Karite butter | 9.200 g |
| Propylene glycol | 2.000 g |
| Methyl para-hydroxybenzoate | 0.075 g |
| Propyl para-hydroxybenzoate | 0.075 g |
| Sterile demineralized water qs | 100.000 g |

(f) A topical gel is prepared by mixing together the following ingredients:

| | |
|---|---|
| Compound of Example 11 | 0.050 g |
| Ethanol | 43.000 g |
| a-Tocopherol | 0.050 g |
| Carboxyvinyl polymer sold under the name "Carbopol 941" by the company "Goodrich" | 0.500 g |
| Triethanolamine as an aqueous solution at 20% by weight | 3.800 g |
| Water | 9.300 g |
| Propylene glycol qs | 100.000 g |

(g) A hair lotion to combat hair loss and to promote the regrowth of hair is prepared by mixing together the following ingredients:

| | |
|---|---|
| Compound of Example 10 | 0.05 g |
| Compound sold under the name "Minoxidil" | 1.00 g |
| Propylene glycol | 20.00 g |
| Ethanol | 34.92 g |
| Polyethylene glycol (molecular mass = 400) | 40.00 g |
| Butylhydroxyanisole | 0.01 g |
| Butylhydroxytoluene | 0.02 g |
| Water qs | 100.00 g |

(h) An anti-acne cream is prepared by mixing together the following ingredients:

| | |
|---|---|
| Compound of Example 13 | 0.050 g |
| Retinoic acid | 0.010 g |
| Mixture of glyceryl stearate and polyethylene glycol stearate (75 mol) sold under the name "Gelot 64" by the company "Gattefosse" | 15.000 g |
| Kernel oil polyoxyethylenated with 6 mol of ethylene oxide, sold under the name "Labrafil M2130 CS" by the company "Gattefosse" | 8.000 g |
| Perhydrosqualene | 10.000 g |
| Preserving agents | qs |
| Polyethylene glycol (molecular mass = 400) | 8.000 g |
| Disodium salt of ethylenediamine-tetraacetic acid | 0.050 g |
| Purified water qs | 100.000 g |

(i) An oil-in-water cream is prepared by making the following fomulation:

| | |
|---|---|
| Compound of Example 9 | 0.020 g |
| Betamethasone 17-valerate | 0.050 g |
| S-carboxymethylcysteine | 3.000 g |
| Polyoxyethylene stearate (40 mol of ethylene oxide) sold under the name "Myrj 52" by the company "Atlas" | 4.000 g |
| Sorbitan monolaurate, polyoxy-ethylenated with 20 mol of ethylene oxide, sold under the name "Tween 20" by the company "Atlas" | 1.800 g |
| Mixture of glyceryl mono- and distearate, sold under the name "Geleol" by the company "Gattefosse" | 4.200 g |
| Propylene glycol | 10.000 g |
| Butylhydroxyanisole | 0.010 g |
| Butylhydroxytoluene | 0.020 g |
| Cetostearyl alcohol | 6.200 g |
| Preserving agents | qs |
| Perhydrosqualene | 18.000 g |
| Mixture of caprylic/capric triglycerides sold under the name "Miglyol 812" by the company "Dynamit Nobel" | 4.000 g |
| Triethanolamine (99% by weight) | 2.500 g |
| Water qs | 100.000 g |

(j) The following oil-in-water type cream is prepared:

| | |
|---|---|
| Lactic acid | 5.000 g |
| Compound of Example 10 | 0.020 g |
| Polyoxyethylene stearate (40 mol of ethylene oxide), sold under the name "Myrj 52" by the company "Atlas" | 4.000 g |
| Sorbitan monolaurate, polyoxyethylenated with 20 mol of ethylene oxide, sold under the name "Tween 20" by the company "Atlas" | 1.800 g |
| Mixture of glyceryl mono- and distearate sold under the name "Geleol" by the company "Gattefosse" | 4.200 g |
| Propylene glycol | 10.000 g |
| Butylhydroxyanisole | 0.010 g |
| Butylhydroxytoluene | 0.020 g |
| Cetostearyl alcohol | 6.200 g |
| Preserving agents | qs |
| Perhydrosqualene | 18.000 g |
| Mixture of caprylic/capric triglycerides sold under the name "Miglyol 812", by the company "Dynamit Nobel" | 4.000 g |
| Water qs | 100.000 g |

What is claimed is:

1. Biaromatic compounds, which have the general formula (I) below:

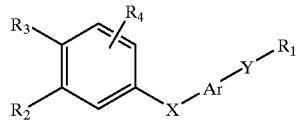
(I)

in which:

$R_1$ represents
- (i) the radical —$CH_3$,
- (ii) the radical —$CH_2$—O—$R_5$,
- (iii) the radical —O—$R_5$,
- (iv) the radical —CO—$R_6$, $R_5$ and $R_6$, having the meanings given below, Y represents a radical chosen from the radicals of formulae (a) and (b) below:

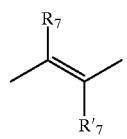
(a)

(b)

$R_7$ and $R'_7$ having the meanings given below,

Ar represents a radical chosen from the radicals of formulae (c) to (f) below:

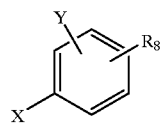
(c)

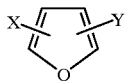
(d)

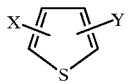
(e)

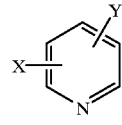
(f)

in which the radical Y is in an ortho or meta position relative to the radical X, X and
Y of these formulae referred to as X and Y in formula (I),
$R_8$ having the meaning given below,
X represents an oxygen or sulphur atom, a radical —SO—, —$SO_2$—, —N($R_9$)— or a radical chosen from the radicals of formulae (g) to (r) below:

(g)

(h)

(i)

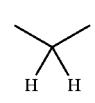
(j)

(k)

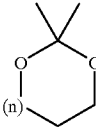
(l)

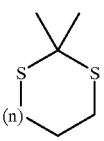
(m)

(n)

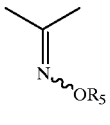
(o)

(p)

(q)

(r)

$R_5$, $R_9$ and n having the meanings given below,
$R_2$ and $R_3$, which may be identical or different, are chosen from the group consisting of:
- (i) a hydrogen atom,
- (ii) an alkyl radical having at least 3 carbon atoms, among which the carbon attached to the phenyl radical of formula (I) is substituted with at least two carbon atoms, (iii) a linear or branched alkyl radical,
(iv) a radical —OR$_5$,
(v) a radical —SR$_5$,
(vi) a polyether radical, wherein R$_2$ and R$_3$, taken together, optionally form, with the adjacent aromatic ring, a 5- or 6-membered ring, optionally substituted with methyl groups and/or optionally interrupted by an oxygen or sulphur atom, with the proviso that, when R$_2$ and R$_3$, as defined above, do not form a ring, at least one of the radicals R$_2$ and R$_3$ has a meaning (ii) mentioned above, R$_4$ and R$_8$, which may be identical or different, represent a hydrogen atom, a halogen atom, a linear or branched alkyl radical, a radical —OR$_5$, a polyether radical, R$_5$ represents a hydrogen atom, a lower alkyl radical or a radical —COR$_{10}$, R$_{10}$ having the meaning given below, R$_6$ represents
(a) a hydrogen atom
(b) a lower alkyl radical
(c) a radical of formula:

R' and R'' having the meanings given below,
(d) a radical —OR$_{11}$
R$_{11}$ having the meaning given below, R$_7$, R'$_7$ and R$_9$, which may be identical or different, represent a hydrogen atom or a lower alkyl radical, n is an integer equal to 0 or 1, R$_{10}$ represents a lower alkyl radical, R$_{11}$ represents a hydrogen atom, a linear or branched alkyl radical, an alkenyl radical, a mono- or polyhydroxyalkyl radical, an aryl or aralkyl radical, optionally substituted, a sugar residue or an amino acid or peptide residue, R$_{12}$ represents a lower alkyl radical, R' and R'', which may be identical or different, represent a hydrogen atom, a lower alkyl radical, a mono- or polyhydroxyalkyl radical, an optionally substituted aryl radical or an amino acid, peptide or sugar residue, or alternatively, taken together, form a heterocycle, and the optical and geometrical isomers of the said compounds of formula (I), as well as their salts.

2. Compounds according to claim 1, wherein they are in the form of salts of an alkali metal or alkaline-earth metal, of zinc, of an organic amine or of an inorganic or organic acid.

3. Compounds according to claim 1, characterized in that the linear or branched alkyl radicals are selected from the group consisting of methyl, ethyl, isopropyl, butyl, tert-butyl, hexyl, nonyl and dodecyl radicals.

4. Compounds according to claim 1, wherein the alkyl radicals having at least 3 carbon atoms, among which the carbon attached to the phenyl radical of formula (I) is substituted with at least two carbon atoms, are chosen from the isopropyl, tert-butyl, 1,1-dimethylhexyl and 1,1-dimethyldecyl radicals.

5. Compounds according to claim 1, wherein the polyhydroxyalkyl radicals are chosen from the group consisting of the 2,3-dihydroxypropyl, 2,3,4-trihydroxybutyl and 2,3,4,5-tetrahydroxypentyl radicals and pentaerythritol residues.

6. Compounds according to claim 1, wherein the aryl radical is a phenyl radical optionally substituted with at least one halogen atom, a hydroxyl radical, an alkyl radical, a nitro function, a methoxy group or an amine function.

7. Compounds according to claim 1, wherein the aralkyl radicals are chosen from the group consisting of the benzyl or phenethyl radicals, optionally substituted with at least one halogen atom, a hydroxyl, a nitro function or a methoxy group.

8. Compounds according to claim 1, wherein the alkenyl radicals are chosen from the group consisting of radicals containing from 2 to 5 carbon atoms and having one or more ethylenic unsaturations, and in particular the allyl radical.

9. Compounds according to claim 1, wherein sugar residue is chosen from the group consisting of glucose, galactose, mannose and glucuronic acid residues.

10. Compounds according to claim 1, wherein the amino acid residues are chosen from the group consisting of residues derived from lysine, from glycine or from aspartic acid.

11. Compounds according to claim 1, wherein the peptide residues are chosen from the group consisting of dipeptide and tripeptide residues.

12. Compounds according to claim 1, wherein the heterocyclic radicals are chosen from the group consisting of piperidino, morpholino, pyrrolidino or piperazino radicals, optionally substituted in position 4 with a C$_1$–C$_6$ alkyl or polyhydroxyalkyl radical.

13. Compounds according to claim 1, characterized in that the polyether radicals are chosen from the methoxymethyl ether, methoxyethoxymethyl ether and methylthiomethyl ether radicals.

14. Compounds according to claim 1, which are selected from the group consisting of:
3-[3-(5,5,8,8-Tetramethyl-5,6,7,8-tetrahydro-2-naphthylcarbonyl)phenyl]acrylic acid;
3-[3-(3,5,5,8,8-Pentamethyl-5,6,7,8-tetrahydro-2-naphthylcarbonyl)phenyl]acrylic acid;
3-[3-(3,5,5,8,8-Pentamethyl-5,6,7,8-tetrahydro-2-naphthylthio)phenyl]acrylic acid;
3-[3-(5,5,8,8-Tetramethyl-5,6,7,8-tetrahydro-2-naphthylthio)phenyl]acrylic acid;
Ethyl 3-{2-[1-(3,5,5,8,8-pentamethyl-5,6,7,8-tetrahydro-2-naphthyl)vinyl]pheny}acryla
3-{2-[1-(3,5,5,8,8-Pentamethyl-5,6,7,8-tetrahydro-2-naphthyl)vinyl]phenyl}acrylate;
Ethyl 3-{3-[1-(3,5,5,8,8-pentamethyl-5,6,7,8-tetrahydro-2-naphthyl)vinyl]phenyl}acrylate;
3-{3-[1-(3,5,5,8,8-Pentamethyl-5,6,7,8-tetrahydro-2-naphthyl)vinyl]phenyl}acrylic acid;
Ethyl 3-{2-[1-(5,5,8,8-tetramethyl-5,6,7,8-tetrahydro-2-naphthyl)vinyl]phenyl}acrylate;
3-{2-[1-(5,5,8,8-Tetramethyl-5,6,7,8-tetrahydro-2-naphthyl)vinyl]phenyl}acrylic acid;
Ethyl 3-{3-[1-(5,5,8,8-tetramethyl-5,6,7,8-tetrahydro-2-naphthyl)vinyl]phenyl}acrylate;
3-{3-[1-(5,5,8,8-Tetramethyl-5,6,7,8-tetrahydro-2-naphthyl)vinyl]phenyl}acrylic acid;
Ethyl 3-{3-[1-(5,5,8,8-tetramethyl-5,6,7,8-tetrahydro-2-naphthyl)ethyl]phenyl}acrylate;
3-{3-[1-(5,5,8,8-Tetramethyl-5,6,7,8-tetrahydro-2-naphthyl)ethyl]phenyl}acrylic acid;
Ethyl 3-{2-[1-(5,5,8,8-tetramethyl-5,6,7,8-tetrahydro-2-naphthyl)ethyl]phenyl}acrylate;
3-{2-[1-(5,5,8,8-Tetramethyl-5,6,7,8-tetrahydro-2-naphthyl)ethyl]phenyl}acrylic acid;
Ethyl 3-{2-[1-(3,5,5,8,8-pentamethyl-5,6,7,8-tetrahydro-2-naphthyl)ethyl]phenyl}acrylate;

3-{2-[1-(3,5,5,8,8-Pentamethyl-5,6,7,8-tetrahydro-2-naphthyl)ethyl]phenyl}acrylic acid;
Ethyl 3-{3-(1-(3,5,5,8,8-Pentamethyl-5,6,7,8-tetrahydro-2-naphthyl)ethyl]phenyl}acrylate acid;
3-{3-(1-(3,5,5,8,8-Pentamethyl-5,6,7,8-tetrahydro-2-naphthyl)ethyl]phenyl}acrylic acid;
Ethyl 3-{2-[1-(5,5,8,8-tetramethyl-5,6,7,8-tetrahydro-2-naphthyl)cyclopropyl]phenyl}-acrylate;
3-{2-[1-(5,5,8,8-Tetramethyl-5,6,7,8-tetrahydro-2-naphthyl)cyclopropyl]phenyl}acrylic acid;
Ethyl 3-{3-[1-(5,5,8,8-tetramethyl-5,6,7,8-tetrahydro-2-naphthyl)cyclopropyl]phenyl}-acrylate;
3-{3-[1-(5,5,8,8-Tetramethyl-5,6,7,8-tetrahydro-2-naphthyl)cyclopropyl]phenyl}acrylic acid;
Ethyl 3-{3-[hydroxyamino-(3,5,5,8,8-pentamethyl-5,6,7,8-tetrahydro-2-naphthyl)methyl]-phenyl}acrylate;
3-{3-(Hydroxyamino-(3,5,5,8,8-pentamethyl-5,6,7,8-tetrahydro-2-naphthyl)methyl]phenyl}acrylic acid;
Ethyl 3-{3-[hydroxyamino-(5,5,8,8-tetramethyl-5,6,7,8-tetrahydro-2-naphthyl)methyl]-phenyl}acrylate;
3-{3-[Hydroxyamino-(3,5,5,8,8-pentamethyl-5,6,7,8-tetrahydro-2-naphthyl)methyl]-phenyl}acrylic acid;
Ethyl 3-{3-[2-(3,5,5,8,8-pentamethyl-5,6,7,8-tetrahydro-2-naphthyl)-[1,3]-dithian-2-phenyl}acrylate;
3-{3-[2-(3,5,5,8,8-Pentamethyl-5,6,7,8-tetrahydro-2-naphthyl)-[1,3]-dithian-2-yl]phenyl}-acrylic acid;
3-{3-(Hydroxylamine-(3,5,5,8,8-pentamethyl-5,6,7,8-tetrahydro-2-naphthyl)methyl]-phenyl}acrylic acid;
Ethyl 3-{3-[hydroxylamine-(5,5,8,8-tetramethyl-5,6,7,8-tetrahydro-2-naphthyl)methyl]-phenyl}acrylate;
3-{2-[Hydroxylamine-(3,5,5,8,8-pentamethyl-5,6,7,8-tetrahydro-2 -naphthyl)methyl]-phenyl}acrylic acid;
Ethyl 3-(2-(Hydroxylamine-(5,5,8,8-tetramethyl-5,6,7,8-tetrahydro-2-naphthyl) methyl]-phenyl}acrylate;
{3-[1-(5,5,8,8-Tetramethyl-5,6,7,8-tetrahydro-2-naphthyl)cyclopropyl]phenyl}propynoic acid;
{3-[1-(3,5,5,8,8-Pentamethyl-5,6,7,8-tetrahydro-2-naphthyl)cyclopropyl]phenyl}propynoic acid;
{2-[1-(5,5,8,8-Tetramethyl-5,6,7,8-tetrahydro-2-naphthyl)cyclopropyl]phenyl}propynoic acid;
{2-[1-(3,5,5,8,8-Pentamethyl-5,6,7,8-tetrahydro-2-naphthyl)cyclopropyl]phenyl}propynoic acid;
3-{2-[1-(3,5,5,8,8-Pentamethyl-5,6,7,8-tetrahydro-2-naphthyl)cyclopropyl]phenyl}acrylic acid;
3-{3-[1-(3,5,5,8,8-Pentamethyl-5,6,7,8-tetrahydro-2-naphthyl)cyclopropyl]phenyl}acrylic acid;
3-{4-Hydroxy-3-(1-(5,5,8,8-tetramethyl-5,6,7,8-tetrahydro-2-naphthyl)cyclopropyl]phenyl}acrylic acid;
3-{3-Hydroxy-2-[1-(5,5,8,8-tetramethyl-5,6,7,8-tetrahydro-2-naphthyl)cyclopropyl]phenyl}acrylic acid;
3-{3-[1-(5,5,8,8-Tetramethyl-5,6,7,8-tetrahydro-2-naphthyl)cyclopropyl]-4-methoxy-phenyl}acrylic acid;
3-{2-[1-(5,5,8,8-Tetramethyl-5,6,7,8-tetrahydro-2-naphthyl)cyclopropyl]-3-methoxy-phenyl}acrylic acid;
3-{4-Hydroxy-3-(1-(3,5,5,8,8-pentamethyl-5,6,7,8-tetrahydro-2-naphthyl)cyclopropyl]-phenyl}acrylic acid;
3-{3-Hydroxy-2-[1-(3,5,5,8,8-pentamethyl-5,6,7,8-tetrahydro-2-naphthyl)cyclopropyl]-phenyl}acrylic acid;
3-{3-[1-(3,5,5,8,8-Pentamethyl-5,6,7,8-tetrahydro-2-naphthyl)cyclopropyl]-4-methoxy-phenyl}acrylic acid;
3-{2-[1-(3,5,5,8,8-Pentamethyl-5,6,7,8-tetrahydro-2-naphthyl) cyclopropyl]-3-methoxy-phenyl}acrylic acid;
3-{3-[1-(5,5,8,8-Tetramethyl-5,6,7,8-tetrahydro-2-naphthyl)cyclopropyl]phenyl}-acrylamide;
3-{2-[1-(5,5,8,8-Tetramethyl-5,6,7,8-tetrahydro-2-naphthyl)cyclopropyl]phenyl}-acrylamide;
3-{3-[1-(3,5,5,8,8-Pentamethyl-5,6,7,8-tetrahydro-2-naphthyl)cyclopropyl]phenyl}-acrylamide;
3-{2-[1-(5,5,8,8-Pentamethyl-5,6,7,8-tetrahydro-2-naphthyl)cyclopropyl]phenyl}-acrylamide;
N-Ethyl-3-{3-[1-(5,5,8,8-tetramethyl-5,6,7,8-tetrahydro-2-naphthyl)cyclopropyl]phenyl}-acrylamide;
N-Ethyl-3-{2-[1-(5,5,8,8-tetramethyl-5,6,7,8-tetrahydro-2 -naphthyl)cyclopropyl]phenyl}-acrylamide;
N-Ethyl-3-{3-[1-(3,5,5,8,8-pentamethyl-5,6,7,8-tetrahydro-2-naphthyl)cyclopropyl]phenyl}-acrylamide;
N-Ethyl-3-{2-[1-(3,5,5,8,8-pentamethyl-5,6,7,8-tetrahydro-2-naphthyl)cyclopropyl)phenyl}-acrylamide;
1-Morpholin-4-yl-3-3-[1-(5,5,8,8-tetramethyl-5,6,7,8-tetrahydro-2-naphthyl)cyclopropyl]-phenyl}propenone;
1-Morpholin-4-yl-3-{2-[1-(5,5,8,8-tetramethyl-5,6,7,8-tetrahydro-2-naphthyl)cyclopropyl]-phenyl}propenone;
1-Morpholin-4-yl -3-{3-[1-(3,5,5,8,8-pentamethyl-5,6,7,8-tetrahydro-2-naphthyl)cyclopropyl]phenyl}propenone;
1-Morpholin-4-yl-3-{2-[1-(3,5,5,8,8-pentamethyl -5,6,7,8-tetrahydro-2-naphthyl)cyclopropyl]phenyl}propenone;
N-(4-Hydroxyphenyl)-3-{3-[1-(5,5,8,8-tetramethyl-5,6,7,8-tetrahydro-2-naphthyl)cyclopropyl]phenyl}acrylamide;
N-(4-Hydroxyphenyl)-3-{2-[1(5,5,8,8-tetramethyl-5,6,7,8-tetrahydro-2-naphthyl)cyclopropyl]phenyl}acrylamide;
N-(4-Hydroxyphenyl)-3-{3-[1-(3,5,5,8,8-pentamethyl-5,6,7,8-tetrahydro-2-naphthyl)cyclopropyl]phenyl}acrylamide;
N-(4-Hydroxyphenyl)-3-{2-[1-(3,5,5,8,8-pentamethyl -5,6,7,8-tetrahydro-2-naphthyl)cyclopropyl]phenyl}acrylamide;
3-{3-[1-(5,5,8,8-Tetramethyl-5,6,7,8-tetrahydro-2-naphthyl)ethyl]phenyl}propenal;
3-{2-[1-(5,5,8,8-Tetramethyl-5,6,7,8-tetrahydro-2-naphthyl)ethyl]phenyl}propenal;
3-{3-[1-(3,5,5,8,8-Pentamethyl-5,6,7,8-tetrahydro-2-naphthyl)ethyl]phenyl}propenal;
3-{2-[1-(3,5,5,8,8-Pentamethyl-5,6,7,8-tetrahydro-2-naphthyl)ethyl]phenyl}propenal;
3-{3-[1-(5,5,8,8-Tetramethyl-5,6,7,8-tetrahydro-2-naphthyl)ethyl]phenyl}prop-2-en-1-ol;
3-{2-[1-(5,5,8,8-Tetramethyl-5,6,7,8-tetrahydro-2-naphthyl)ethyl]phenyl}prop-2-en-1-ol;
3-{3-[1-(3,5,5,8,8-Pentamethyl-5,6,7,8-tetrahydro-2-naphthyl)ethyl]phenyl}prop-2-en-1-ol;
3-{2-[1-(3,5,5,8,8-Pentamethyl-5,6,7,8-tetrahydro-2-naphthyl)ethyl]phenyl}prop-2-en-1-ol; and mixtures thereof.

15. Compounds according to claim 1, which they have at least one of the following characteristics:
$R_1$ represents the radical —CO—$R_6$
Ar represents the radicals of formula (c) or (f)
X represents the radicals of formula (g), (h), (n) or (m)
$R_2$ and $R_3$, taken together, form, with the adjacent aromatic ring, a 5- or 6-membered ring optionally substituted with methyl groups and/or optionally interrupted by an oxygen or sulphur atom.

16. The alkaline salt of claim 2, which is a zinc salt.

17. The compounds of claim 1, wherein X is not a radical (g), (j) or (k).

18. The compounds of claim 1, wherein X is not a radical —O—, —SO—, —SO$_2$—, or NR$_9$.

19. The compounds of claim 1 which possess agonist activity for RXR receptors.

20. The compounds of claim 1, which possess antagonist activity for RXR receptors.

21. A pharmaceutical or cosmetic composition comprising a pharmaceutically or cosmetically effective amount of a compound according to claim 1.

22. A pharmaceutical composition which comprises a therapeutically effective amount of at least one compound according to claim 1, or a pharmaceutically acceptable salt or isomer thereof, and a pharmaceutically acceptable vehicle, carrier, or diluent therefor.

23. The pharmaceutical composition of claim 22, wherein the composition of said compound is between 0.001% and 5% by weight relative to the weight of the composition as a whole.

24. A cosmetic composition which comprises a cosmetically effective amount of at least one compound according to claim 1, or a cosmetically acceptable salt or isomer thereof which is comprised in a cosmetically acceptable vehicle, carrier or diluent therefor.

25. The composition according to claim 23, wherein the concentration of said compound ranges from 0.001% to 3% by weight relative to the weight of the composition as a whole.

* * * * *